(12) United States Patent
Hanson et al.

(10) Patent No.: US 10,286,100 B2
(45) Date of Patent: May 14, 2019

(54) MEDICAL DRESSINGS COMPRISING FLUID MANAGEMENT ARTICLES AND METHODS OF USING SAME

(71) Applicant: 3M INNOVATIVE PROPERTIES COMPANY, Saint Paul, MN (US)

(72) Inventors: Jennifer N. Hanson, Saint Paul, MN (US); Ibrahim A. El-Hedok, Woodbury, MN (US); Hassan Sahouani, Hastings, MN (US); Bradley W. Eaton, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 15/514,670

(22) PCT Filed: Sep. 28, 2015

(86) PCT No.: PCT/US2015/052648
§ 371 (c)(1),
(2) Date: Mar. 27, 2017

(87) PCT Pub. No.: WO2016/053875
PCT Pub. Date: Apr. 7, 2016

(65) Prior Publication Data
US 2017/0216476 A1    Aug. 3, 2017

Related U.S. Application Data

(60) Provisional application No. 62/058,386, filed on Oct. 1, 2014.

(51) Int. Cl.
| | |
|---|---|
| *A61L 15/26* | (2006.01) |
| *C08L 71/02* | (2006.01) |
| *C09D 133/06* | (2006.01) |
| *A61L 15/16* | (2006.01) |
| *A61L 15/44* | (2006.01) |
| *C08L 33/08* | (2006.01) |

(52) U.S. Cl.
CPC .............. *A61L 15/26* (2013.01); *A61L 15/16* (2013.01); *A61L 15/44* (2013.01); *C08L 33/08* (2013.01); *C08L 71/02* (2013.01); *C09D 133/06* (2013.01)

(58) Field of Classification Search
CPC .......... A61L 15/26; A61L 15/16; A61L 15/44; C08L 33/08
USPC ....................................................... 424/443
See application file for complete search history.

(56) References Cited

U.S. PATENT DOCUMENTS

| | | |
|---|---|---|
| RE24,906 E | 12/1960 | Ulrich |
| 3,389,827 A | 6/1968 | Abere |
| 3,645,835 A | 2/1972 | Hodgson |
| 4,112,213 A | 9/1978 | Waldman |
| 4,310,509 A | 1/1982 | Berglund |
| 4,323,557 A | 4/1982 | Rosso |
| 4,429,001 A | 1/1984 | Kolpin |
| 4,595,001 A | 6/1986 | Potter |
| 4,737,410 A | 4/1988 | Kantner |
| 4,755,178 A | 7/1988 | Insley |
| 5,088,483 A * | 2/1992 | Heinecke .............. A61F 13/023 128/849 |
| 5,531,855 A | 7/1996 | Heinecke |
| 6,048,908 A | 4/2000 | Kitagawa |
| 6,264,976 B1 | 7/2001 | Heinecke |
| 6,838,589 B2 | 1/2005 | Liedtke |
| 6,881,875 B2 | 4/2005 | Swenson |
| 6,977,323 B1 | 12/2005 | Swenson |
| 7,005,143 B2 | 2/2006 | Abuelyaman |
| 7,030,288 B2 | 4/2006 | Liedtke |
| 7,612,248 B2 | 11/2009 | Burton |
| 7,947,366 B2 | 5/2011 | Ishiwatari |
| 2006/0096911 A1 | 5/2006 | Brey |
| 2008/0233348 A1 | 9/2008 | Ishiwatari |
| 2009/0187130 A1 | 7/2009 | Asmus |
| 2010/0068525 A1 | 3/2010 | Jung |
| 2010/0104647 A1 | 4/2010 | Ting |
| 2010/0311850 A1* | 12/2010 | Wickert ................ B01D 15/00 521/61 |
| 2010/0318048 A1* | 12/2010 | Hoefinghoff ............ A61L 15/32 604/365 |

(Continued)

FOREIGN PATENT DOCUMENTS

| | | |
|---|---|---|
| EP | 0156649 | 10/1985 |
| EP | 0341870 | 11/1989 |
| EP | 2545976 | 8/2016 |

(Continued)

OTHER PUBLICATIONS

International Search Report for PCT International Application No. PCT/US2015/052648, dated Jan. 25, 2016, 5 pages.
International Search Report for PCT International Application No. PCT/US2015/052564, dated Jan. 4, 2016, 4 pages.

*Primary Examiner* — Yanzhi Zhang
(74) *Attorney, Agent, or Firm* — 3M Innovative Properties Company; Trisha D. Adamson

(57) ABSTRACT

Medical dressings and methods of using same. The medical dressing can include a fluid management article. The fluid management article can include a fibrous substrate and porous polymeric particles. At least 50% of the porous polymeric particles are bound to the fibrous substrate. Methods of using the medical dressings can include applying the medical dressing to the target site, such that the fluid management article is in fluid communication with the target site.

16 Claims, 7 Drawing Sheets

(56) References Cited

U.S. PATENT DOCUMENTS

2011/0123456 A1    5/2011  Pandit
2014/0309314 A1  10/2014  Sahouani

FOREIGN PATENT DOCUMENTS

| WO | 2007-075442 | 7/2007 |
| --- | --- | --- |
| WO | 2007-075508 | 7/2007 |
| WO | 2007-146722 | 12/2007 |
| WO | 2010-056541 | 5/2010 |
| WO | 2010-056543 | 5/2010 |
| WO | 2010-056544 | 5/2010 |
| WO | 2013-077981 | 5/2013 |
| WO | 2014-099709 | 6/2014 |
| WO | 2014-186328 | 11/2014 |
| WO | 2014-186336 | 11/2014 |
| WO | 2015-095100 | 6/2015 |
| WO | 2016-053830 | 4/2016 |

* cited by examiner

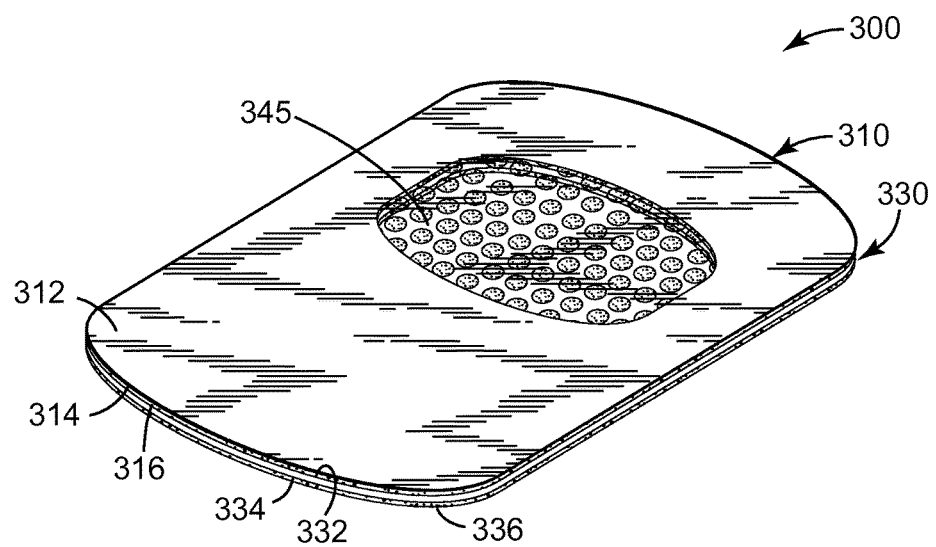
FIG. 3
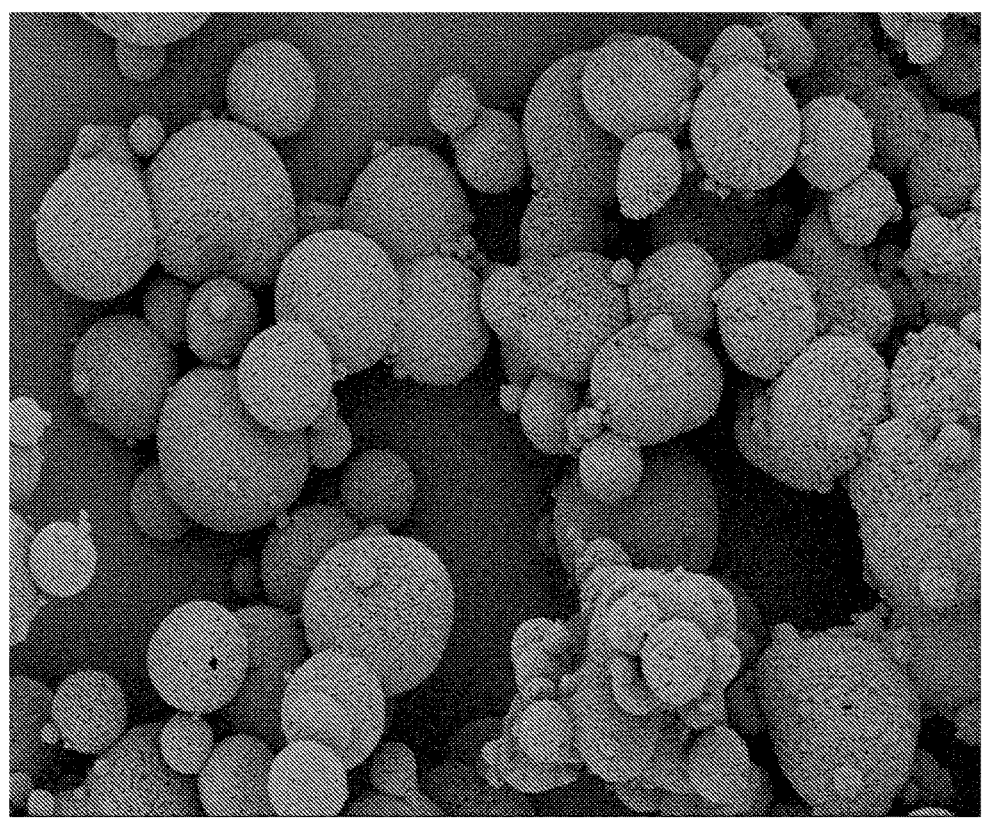
FIG. 4     60.0μm

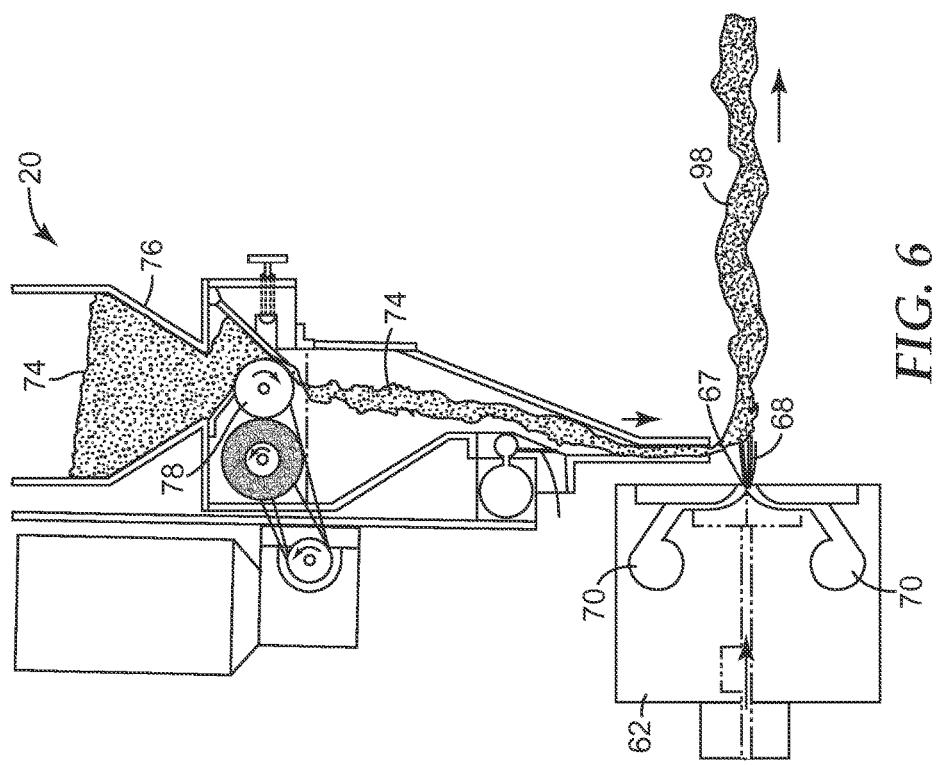

*FIG. 7*  100μm
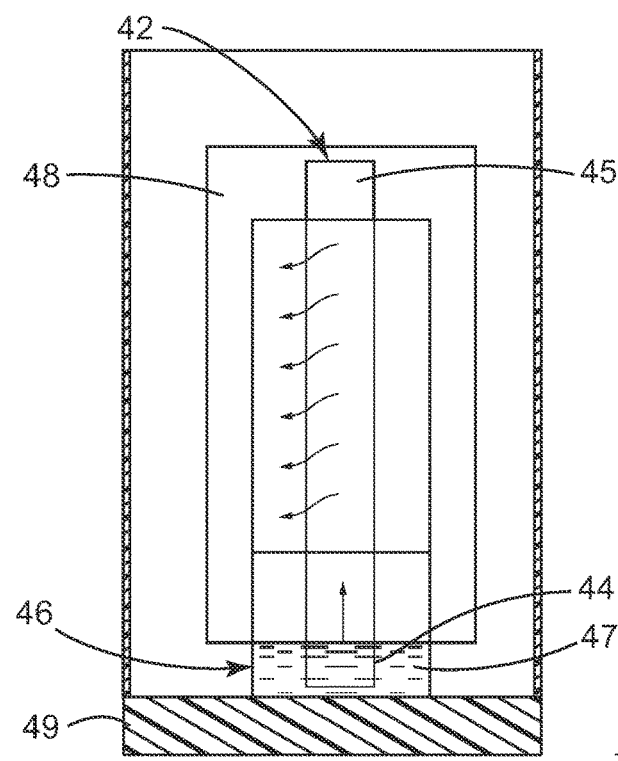
*FIG. 8*

MEDICAL DRESSINGS COMPRISING FLUID MANAGEMENT ARTICLES AND METHODS OF USING SAME

CROSS REFERENCE TO RELATED APPLICATIONS

This application is a national stage filing under 35 U.S.C. 371 of PCT/US2015/052648, filed Sep. 28, 2015, which claims the benefit of U.S. Provisional Application No. 62/058,386, filed Oct. 1, 2014, the disclosures of which are incorporated by reference in their entirety herein.

FIELD

The present disclosure generally relates to medical dressings, such as wound dressings or IV dressings, and particularly, to medical dressings comprising fluid management articles for effective fluid management.

BACKGROUND

Medical adhesive dressings are used for a variety of medical applications. Adhesive dressings can provide barrier protection from infectious species to a wound or catheter insertion site. Transparent adhesive dressings are commonly used at a catheter insertion site because visual monitoring of the site can be achieved without removing the dressing.

It is often desired to have a medical dressing with fluid management properties, e.g. having the ability to absorb, wick, and evaporate fluids. These properties are desired for applications where continuous fluids management is needed, such as at wound sites or at intravenous (IV) sites.

Cellulosic nonwovens have the ability to absorb and wick water, for instance; however, they tend to hold on to water and often lose their structural integrity. Other super absorbing materials, e.g. sodium polyacrylate fibers, can absorb high levels of moisture, yet undergo significant swell that leads to dimensional changes in the material.

Various polymeric particles having pores have been prepared. Some of these have been used, for example, as ion exchange resins or other chromatographic resins. Others have been used, for example, to adsorb and/or deliver different active agents. Such particles are described, for example, in U.S. Patent Application 2010/0104647 (Ting), U.S. Patent Application Publication 2011/0123456 (Pandidt et al.), U.S. Pat. No. 6,048,908 (Kitagawa), and Patent Application Publications WO 2013/077981 (Sahouani), WO 2007/075508 (Rasmussen et al.), and WO 2007/075442 (Ramussen et al.).

SUMMARY

Medical dressings are provided comprising fluid management articles, or porous articles for transporting fluid away from a target source or site, and particularly, for wicking and evaporating fluids. Fluid management articles are provided that include a fibrous substrate and porous polymeric particles bound to the fibrous substrate. Such fluid management articles can optionally contain a biologically active agent.

Some aspects of the present disclosure provide a medical dressing. The medical dressing can include a fluid management article. The fluid management article can include 1) a fibrous substrate; and 2) porous polymeric particles, wherein at least 50% of the porous polymeric particles are bound to the fibrous substrate. The porous polymeric particles can include a polymerized product of a reaction mixture comprising: a) a first phase having a first volume and comprising i) a compound of Formula (II)

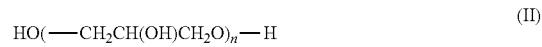

wherein n is an integer equal to at least 1, and ii) a nonionic surfactant; and b) a second phase having a second volume and being dispersed in the first phase, wherein the first volume is greater than the second volume. The second phase can include i) a monomer composition comprising at least 10 weight percent of a first monomer of Formula (I)

based on a total weight of the monomer composition, wherein p is an integer equal to at least 1 and $R^1$ is hydrogen or alkyl, and ii) a poly(propylene glycol) having a weight average molecular weight of at least 500 grams/mole, wherein the poly(propylene glycol) does not form a portion of the polymerized product.

In one embodiment, the reaction mixture used to form the porous polymeric particles can include (a) a first phase and (b) a second phase dispersed in the first phase, wherein a volume of the first phase is greater than a volume of the second phase. The first phase contains (i) a compound of Formula (II)

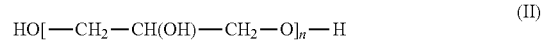

where the variable n is an integer equal to at least 1 and (ii) a nonionic surfactant. The second phase contains (i) a monomer composition containing at least 10 weight percent of the first monomer of Formula (I)

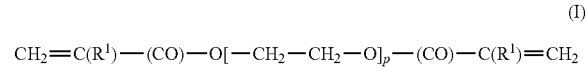

based on the total weight of the monomer composition and (ii) the poly(propylene glycol) having a weight average molecular weight of at least 500 grams/mole. In Formula (I), the variable p is an integer equal to at least 1 and the group $R^1$ is hydrogen or methyl.

Other features and aspects of the present disclosure will become apparent by consideration of the detailed description and accompanying drawings.

BRIEF DESCRIPTION OF THE DRAWINGS

FIG. 3 is a schematic perspective view of a medical dressing according to another embodiment of the present disclosure.

FIG. 4 is a scanning electron micrograph (SEM) of porous polymeric particles prepared as described in Preparatory Example 1.

FIG. 6 is a schematic cross-sectional view of a meltblowing apparatus for making fluid management articles.

FIG. 7 is a scanning electron micrograph of the article of Example 1.

FIG. 8 is a schematic of the experimental setup described in the Wicking/Evaporation Performance Testing examples.

DETAILED DESCRIPTION

Figure 1:
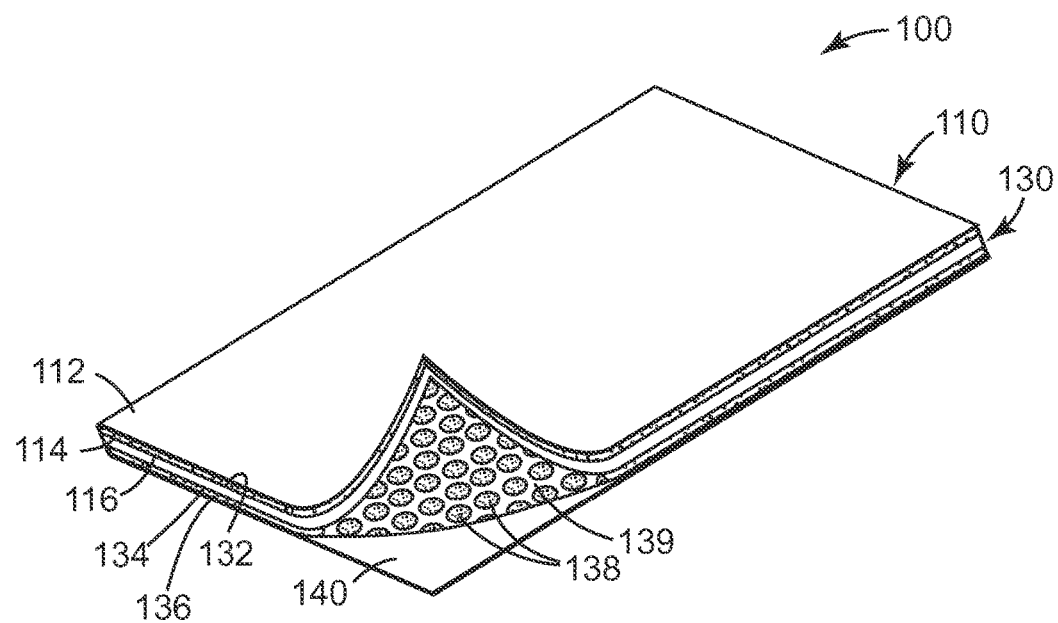
FIG. 1 is a schematic perspective view of a medical dressing according to one embodiment of the present disclosure.

The present disclosure generally relates to medical dressings comprising one or more fluid management articles. Fluid management articles of the present disclosure include a fibrous substrate and porous polymeric particles bound to the fibrous substrate. More particularly, the fluid management articles of the present disclosure can particularly be used for wicking and evaporating fluids, and can optionally contain an antimicrobial agent.

Both the porous polymeric particles and the fibrous substrate have voids or free volume. The voids in the fibrous substrate allow fluid to wick across a length of the substrate and come into contact with the porous polymeric particles bound to the fibrous substrate. The porous polymeric particles have pores on its outer surface and, at least in some embodiments, can have hollow interiors. The terms "porous polymeric particle," "polymeric particle," and "porous particle" are used interchangeably.

Medical dressings of the present disclosure can include a variety of types of dressings, including, but not limited to, low to highly exudating wound dressings, minor wound bandages intravenous (IV) dressings, compression dressings, or combinations thereof.

In the medical dressings of the present disclosure, the fluid management article can be positioned to transport fluid (e.g., blood, wound exudate, sweat, or a combination thereof) away from a target site, such as a minor to severe wound, a skin graft donor site, a pressure ulcer, between folds of skin, a catheter insertion site, or a combination thereof. Target sites can include sites that are desired to be visualized during the course of a treatment, such as an insertion site, as described in greater detail below with respect to FIG. 3.

Definitions

The term "a", "an", and "the" are used interchangeably with "at least one" to mean one or more of the elements being described.

The term "and/or" means either or both. For example "A and/or B" means only A, only B, or both A and B.

The terms "including," "comprising," and "having," and variations thereof, are meant to encompass the items listed thereafter, and equivalents thereof, as well as additional items.

Unless specified or limited otherwise, the terms "supported," and "coupled" and variations thereof are used broadly and encompass both direct and indirect supports and couplings.

The terms "polymer" and "polymeric material" are used interchangeably and refer to materials formed by reacting one or more monomers. The terms include homopolymers, copolymers, terpolymers, or the like. Likewise, the terms "polymerize" and "polymerizing" refer to the process of making a polymeric material that can be a homopolymer, copolymer, terpolymer, or the like. The terms "copolymer" and "copolymeric material" refer to a polymeric material prepared from at least two monomers.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "aryl" refers to a monovalent group that is aromatic and carbocyclic. The aryl ("Ar") can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The terms "room temperature" and "ambient temperature" are used interchangeably to mean a temperature in the range of 20° C. to 25° C.

The term "bound", relating to porous polymeric particles being bound to one or more fibers of the fibrous substrate, means being attached by being fused or by being adhered using an adhesive or polymeric binder, as opposed to being held by physical interactions (for example, adsorption or mechanical entrapment). The polymeric binder excludes binder fibers, such as the binder fibers typically employed in wet-laying techniques.

The term "fused" means directly connected together. Often, porous polymeric particles are fused to the fibrous substrate by heating the fibrous substrate to a temperature above the glass transition temperature of the fibers, contacting the particles with the heated substrate, and cooling the particles and substrate. After cooling, porous polymeric particles are directly connected to the fibrous substrate.

The term "monomer composition" refers to that portion of a polymerizable composition that includes the monomers and only the monomers. More specifically, the monomer composition includes at least the first monomer of Formula (I). The term "reaction mixture" includes, for example, the monomer composition, the poly(propylene glycol), any other components such as those included in the first phase and the second phase described below. Following polymerization, the mixture can be referred to as a "polymerized product mixture" that comprises the polymerized product (i.e., the particles) and any other components. Some of the components in the reaction mixture but may not undergo a chemical reaction or form a portion of the polymerized product, but can influence the chemical reaction and the resulting polymeric material. Such components may not be present in the resulting fluid management article. For example, the poly(propylene glycol is removed from the polymerized product mixture to provide the porous polymeric particles, such that the poly(propylene glycol) does not form a portion of the polymerized product, even if present in the polymerized product mixture. In some embodiments, the resulting porous polymeric particles are substantially free of poly(propylene glycol).

The term "meltblown process" refers to making fine fibers by extruding a thermoplastic polymer through a die consisting of one or more holes. As the fibers emerge from the die they are attenuated by an air stream that is run more or less in parallel or at a tangent to the emerging fibers.

FIG. 1 illustrates a medical dressing 100 according to one embodiment of the present disclosure. The medical dressing 100 includes a backing 110 and a fluid management article 130 comprising a fibrous substrate and porous polymeric particles.

The backing 110 can include a first (or top) major surface 112 and a second (or bottom) major surface 114 opposite the first major surface 112. The second major surface 114 can be configured to be applied to skin. The second major surface 114 can include a backing adhesive (or a first adhesive) 116. The backing adhesive 116 can be applied to at least a portion of the second major surface 114 and need not entirely cover the second major surface 114. In some embodiments, as shown in FIG. 1, the backing adhesive 116 can be coextensive with the second major surface 114.

The backing 110 is typically thin, flexible and conformable to a skin surface. The fluid management article 130 can provide structural reinforcement and support to the backing 110, which can inhibit the backing 110 from folding, wrinkling or folding over and adhering to itself. In some embodiments, the backing 110 can be formed of a variety materials, including materials which provide resiliency, high moisture vapor permeability and/or transparency.

In some embodiments, the backing 110 need not include the backing adhesive 116 and, for example, can include a compression dressing (or wrap) that can be wrapped around the fluid management article 130 (e.g., around a limb) to hold the fluid management article 130 at a desired location, i.e., over a target site. Various additional details regarding backings of the present disclosure are described in greater detail below.

As described in greater detail below, the fluid management article 130 can include a) porous polymeric particles and b) a fibrous porous matrix (or "fibrous substrate"), wherein the porous polymeric particles are distributed throughout the fibrous porous matrix.

The fluid management article 130 can include a first (or top) major surface 132 and a second (or bottom) major surface 134 opposite the first major surface 132. The second major surface 134 is configured to be applied to skin. The backing 110 and the fluid management article 130 are arranged in an overlapping fashion, such that at least a portion of the second major surface 114 of the backing 110 is coupled to (e.g., adhered to) at least a portion of the first major surface 132 of the fluid management article 130 (e.g., via the backing adhesive 116). By way of example, in the medical dressing 100 of FIG. 1, the backing 110 and the fluid management article 130 are coextensive with one another.

In some embodiments, as shown in FIG. 1, the second major surface 134 can include a skin-contact adhesive (or a second adhesive) 136. The skin-contact adhesive 136 can be applied to at least a portion of the second major surface 134 and need not entirely cover the second major surface 134.

Various additional details regarding fluid management articles of the present disclosure are described in greater detail below.

In some embodiments, the backing 110 and the fluid management article 130 can be permanently coupled (e.g., adhered or bonded) together, such that they are inseparable, i.e., without causing damage to one or both of the backing 110 and the fluid management article 130. In such embodiments, the backing adhesive 116 can be a more aggressive adhesive with higher or greater adhesion than the skin-contact adhesive 136.

In some embodiments, as shown in FIG. 1, the skin-contact adhesive 136 can be patterned (e.g., pattern coated) to include discrete portions or islands 138 and one or more gaps 139 therebetween. Such a patterned adhesive can provide channels or pathways for fluid (e.g., wound exudates, blood, etc.) from a target site (e.g., a wound, an insertion site, etc.) into the fluid management article 130 for fluid transport, i.e., wicking and/or evaporation.

Additional details regarding patterned adhesives can be found in U.S. Pat. No. 7,947,366 ("the '366 patent"), which is incorporated by reference herein in its entirety.

For example, to retain the pattern in the adhesive 136 over time, the adhesive 136 can include a pressure-sensitive adhesive with a recovery percent of at least 35%, as measured according to the Compliance Creep Test provided in the Examples section of the '366 patent. Adhesives formulated with a recovery percent of at least 35% can retain the pattern of the adhesive over time. By "time," it is generally meant that the adhesive does not flow for at least 19 days at 66° C., and in some embodiments, does not flow for at least 57 days at 66° C.

In some embodiments, the backing adhesive 116 can also be patterned, for example, in embodiments in which the backing adhesive 116 is positioned in direct contact with skin. Examples of such embodiments are described below with reference to FIGS. 2 and 3. In some embodiments, as shown in FIG. 3, such a backing adhesive can be positioned to provide a fluid pathway from a target site to the fluid management article, such that the fluid management article is still in fluid communication with the target site even if not applied directly over the target site.

In some embodiments, the skin-contact adhesive 136 can be present or provided by at least the second major surface 134 of the fluid management article 130, but may also be present in other portions (e.g., throughout at least a portion of the volume) of the fluid management article 130. In some embodiments, the adhesive 136 is not a separate coating or element added to the fluid management article 130 in a secondary step, but rather, the fluid management article 130 itself can include or provide necessary tack. For example, in some embodiments, pressure-sensitive adhesive fibers or fibers that have inherent tackiness can be added during the process of making the fibrous substrate (e.g., during a meltblown process). In such embodiments, the fluid management article 130 can still be considered to include or comprise the skin-contact adhesive 136, e.g., on at least the second major surface 134.

In embodiments employing adhesive fibers, adhesive fibers can contain an extrudable pressure-sensitive adhesive material suitable for melt blowing (e.g., a material having an apparent viscosity from 150 to 800 poise under melt-processing conditions, measured by a capillary rheometer), fiber spinning, or spunbond processing. In some embodiments, the fibers in the fibrous substrate can include pressure-sensitive adhesive fibers that will impart durable tackiness to the fluid management article 130 and can provide sufficient adhesion to serve as the skin-contact adhesive 136.

With conjugate fibers or co-formed fibers of different polymers or blends formed from a single die or spinneret, the viscosities of the separate polymer flowstreams should be fairly closely matched for uniform fiber and web formation, but this is not required. In general, matching viscosities will ensure more uniformity in the conjugate fibers by minimizing polymer mixing, which mixing can result in fiber breakage and formation of shot (small particulate polymer material), and lower web tensile properties. However, the presence of discontinuous fibers or shot is not necessarily undesirable as long as the web has the desired overall tensile and cohesive strength, and desired adhesive properties.

In some embodiments, the backing 110, the backing adhesive 116, and the skin-contact adhesive 136 need not be employed, and instead, the medical dressing 100 can include the fluid management article 130 alone. That is, in some embodiments, the medical dressing 100 can include the fluid management article 130 alone, with no additional components. Such a dressing can be used, for example, as an absorptive wipe or could be placed within the recesses or folds of skin to manage moisture.

In some embodiments, the backing 110 and the fluid management article 130 can be separately provided, for example, one or both of the backing 110 and the fluid management article 130 can be provided in a roll, and a desired amount (e.g., length) of one or both can be cut or separated from the roll to form a customized medical dressing. In such embodiments, one or both of the backing 110 and the fluid management article 130 may not include any adhesive, i.e., the dressing may be free of the backing adhesive 116 and/or the skin-contact adhesive 136. For example, as mentioned above, the fluid management article 130 (e.g., adhesive or non-adhesive) can be positioned in a desired location, and a backing (e.g., adhesive or non-adhesive) can be wrapped around the fluid management article 130 (e.g., around a limb) to hold the fluid management article 130 in place.

Thus, while the backing 110, the backing adhesive 116, the fluid management article 130 and the skin-contact adhesive 136 are each shown by way of example in FIG. 1, it should be understood that, in some embodiments, the dressing 100 can include the fluid management article 130 alone, or the fluid management article 130 in combination with one or more of the backing 110 (with or without the backing adhesive 116) and the adhesive 136. That is, in some embodiments, the dressing 100 can include the fluid management article 130 and the adhesive 136; the backing 110 and the fluid management article 130; the backing 110, the backing adhesive 116, and the fluid management article 136; the backing 110, the fluid management article 130, and the adhesive 136; or the backing 110, the backing adhesive 116, the fluid management article 130, and the adhesive 136.

As shown in FIG. 1, the medical dressing 100 can further include one or more release liners 140 positioned to cover any exposed adhesives (i.e., the skin-contact adhesive 136) prior to use. Examples of release liners suitable for use with medical dressings of the present disclosure are described below.

In addition, the medical dressings of the present disclosure can optionally include any combination of tabs, or a frame or carrier layer to support the medical dressing, e.g., during handling and application. Such tabs, frames or carriers can be coupled to, and positioned over at least a portion of, the first major surface 112 of the backing 110. Examples of tabs are described in U.S. Pat. No. 5,088,483, which is incorporated herein by reference in its entirety. Examples of a frame or carrier layer are described in U.S. Publication No. 2009/0187130 and PCT Publication No. WO 2014/099709, each of which is incorporated herein by reference in its entirety.

In some embodiments, a low adhesion (low adhesion backsize or LAB) coating may be provided on the first major surface 112 of the backing 110 at least in a region that comes in contact with any tabs, frames or carrier layers. The low adhesion coating can reduce the need to change the entire medical dressing 100 (or the backing 110) due to unwanted dressing removal when other tapes or devices are placed on the medical dressing 100 (or the backing 110) and removed, and can also reduce the surface friction of the medical dressing 100 on bed linens or other fabrics, thereby offering additional protection against the accidental removal of medical dressing 100. A description of a low adhesion backing material suitable for use with medical dressings of the present disclosure can be found in U.S. Pat. Nos. 5,531,855 and 6,264,976, which are incorporated herein by reference in their entirety.

Figure 2:
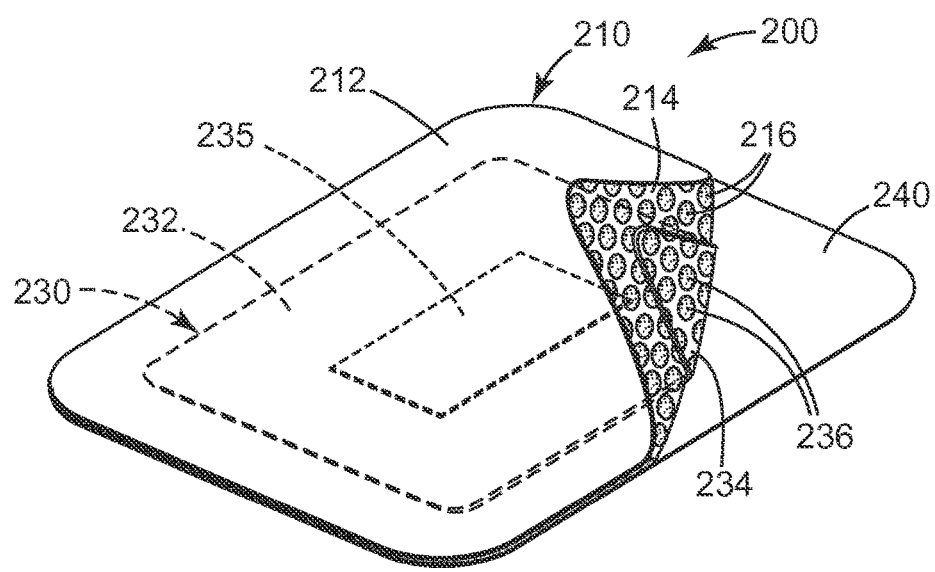
FIG. 2 is a schematic perspective view of a medical dressing according to another embodiment of the present disclosure.

Additional exemplary embodiments of medical dressings of the present disclosure will now be described with respect to FIGS. 2 and 3. FIGS. 2 and 3 each illustrate various medical dressings of the present disclosure, wherein like numerals represent like elements. The medical dressings of FIGS. 2 and 3 share many of the same elements, features, and functions as the medical dressing 100 described above with respect to FIG. 1. Reference is made to the description above accompanying FIG. 1 (and the description below regarding specific components of the medical dressing, such as the fluid management article) for a more complete description of the features and elements (and alternatives to such features and elements) of the embodiments illustrated in FIGS. 2 and 3. Any of the features or elements described above with respect to FIG. 1 can be applied to the embodiments of FIGS. 2 and 3, and vice versa.

FIG. 2 illustrates a medical dressing 200 according to another embodiment of the present disclosure. The medical dressing 200 includes a backing 210 and a fluid management article 230 comprising a fibrous substrate and porous polymeric particles.

The backing 210 can include a first (or top) major surface 212 and a second (or bottom) major surface 214 opposite the first major surface 212. The second major surface 214 can include a backing adhesive 216. The backing adhesive 216 can be applied to at least a portion of the second major surface 214 and need not entirely cover the second major surface 214. As shown in FIG. 2, the backing adhesive 216 is coextensive with the second major surface 214.

The fluid management article 230 can include a first (or top) major surface 232 and a second (or bottom) major surface 234 opposite the first major surface 212. The backing 210 and the fluid management article 230 are arranged in an overlapping fashion, such that at least a portion of the second major surface 214 of the backing 210 is coupled to (e.g., adhered to) at least a portion of the first major surface 232 of the fluid management article 230 (e.g., via the backing adhesive 216). In addition, in some embodiments, the backing 210 and the fluid management article 230 can be permanently coupled (e.g., adhered or bonded) together, such that they are inseparable, i.e., without causing damage to one or both of the backing 210 and the fluid management article 230.

The second major surface 234 can include a skin-contact adhesive 236. The skin-contact adhesive 236 can be applied to at least a portion of the second major surface 234 and need not entirely cover the second major surface 234. In some embodiments, as shown in FIG. 2, the skin-contact adhesive 236 can be patterned (e.g., pattern coated), as described above.

In some embodiments, as shown in FIG. 2, the backing adhesive 216 can also be patterned. As shown in FIG. 2, the medical dressing 200 is illustrated by way of example as an island dressing, where the size (i.e., area) of the fluid management article 230 is less than that of the backing 210, such that the backing 210 includes at least a portion that extends beyond an edge of the fluid management article 230, and in some embodiments, extends beyond an entire periphery of the fluid management article 230. In such embodiments, at least a portion of the backing adhesive 216 is positioned to contact skin when the medical dressing 200 is coupled to skin. In such embodiments, the backing adhesive 216 can also be a skin-contact adhesive, and can also be patterned (e.g., pattern coated) to facilitate fluid movement away from the skin surface and into the fluid management article 230.

As further shown in FIG. 2, the medical dressing 200 (or any medical dressing of the present disclosure) can further include one or more absorbent cores (or bodies) 235 (such as foams or gels (e.g., hydrogels)) positioned to absorb fluid from a target site, which can facilitate drawing fluid into the fluid management article 230 for wicking and/or evaporation. In some embodiments, as shown, the absorbent core 235 can be adhered to the second major surface 234 of the fluid management article 230 via the adhesive 236. In such embodiments, the absorbent core 235 is coupled to the fluid management article 230 (i.e., on a skin-facing side), and the fluid management article 230 is coupled to the backing 210 (i.e., on a skin-facing side). In some embodiments, the absorbent core 235 can be adhered to at least one of the fluid management article 230 and the backing 210 (e.g., overlapping an edge of the fluid management article 230). In some embodiments, the absorbent core 235 can be positioned between the backing 210 and the fluid management article 230, i.e., between the second major surface 214 of the backing 210 and the first major surface 232 of the fluid management article 230. Still, other configurations are possible and within the spirit and scope of the present disclosure. Suitable absorbent cores of the present disclosure are described in greater detail below.

As shown in FIG. 2, the medical dressing 200 can further include one or more release liners 240 positioned to cover any exposed adhesives prior to use. As a result of the island dressing configuration of the medical dressing 200, both the skin-contact adhesive 236 and the backing adhesive 216 (which may also be a suitable skin-contact adhesive) are exposed on an overall bottom or back surface of the medical dressing 200, and the one or more release liners 240 can be configured to cover both the skin-contact adhesive 236 and the backing adhesive 216.

As mentioned above with respect to FIG. 1, the medical dressing 200 need not include any or all of the backing 210, the backing adhesive 216, the skin-contact adhesive 236, or the absorbent core 235.

For example, in some embodiments, the medical dressing 200 may not include the backing 110 or the backing adhesive 116. In such embodiments, the fluid management article 230 can be the outermost layer of the dressing, and the medical dressing 200 can still be an "island dressing" if the absorbent core 235 is employed and the fluid management article 230 is sized to be greater than the size of the absorbent core 235, as shown in FIG. 2. Such medical dressings can be used, e.g., to cover minor to moderate exuding wounds. However, in some embodiments, the absorbent core 235, if employed, can have the same size (e.g., area) as the fluid management article 230.

As described above, the medical dressing 200 can further include any combination of tabs, frames or carrier layers to support the medical dressing, e.g., during handling and application.

FIG. 3 illustrates a medical dressing 300 according to another embodiment of the present disclosure. The medical dressing 300 includes a backing 310 and a fluid management article 330 comprising a fibrous substrate and porous polymeric particles.

The backing 310 can include a first (or top) major surface 312 and a second (or bottom) major surface 314 opposite the first major surface 312. The second major surface 314 can include a backing adhesive 316. The backing adhesive 316 can be applied to at least a portion of the second major surface 314 and need not entirely cover the second major surface 314. As shown in FIG. 3, the backing adhesive 316 is coextensive with the second major surface 314.

The fluid management article 330 can include a first (or top) major surface 332 and a second (or bottom) major surface 334 opposite the first major surface 312. The backing 310 and the fluid management article 330 are arranged in an overlapping fashion, such that at least a portion of the second major surface 314 of the backing 310 is coupled to (e.g., adhered to) at least a portion of the first major surface 332 of the fluid management article 330 (e.g., via the backing adhesive 316). In addition, in some embodiments, the backing 310 and the fluid management article 330 can be permanently coupled (e.g., adhered or bonded) together, such that they are inseparable, i.e., without causing damage to one or both of the backing 310 and the fluid management article 330.

The second major surface 334 can include a skin-contact adhesive 336. The skin-contact adhesive 336 can be applied to at least a portion of the second major surface 334 and need not entirely cover the second major surface 334. In some embodiments, the skin-contact adhesive 336 can be patterned (e.g., pattern coated), as described above.

In some embodiments, as shown in FIG. 3, the backing adhesive 316 can also be patterned. As shown in FIG. 3, the medical dressing 300 is illustrated by way of example as an intravenous (IV) dressing, configured to be positioned over an insertion site (e.g., for any of a variety of IV-based medical articles or catheters). As such, it can be necessary to maintain visibility of the insertion site, even while the medical dressing 300 is coupled to the skin over the insertion site. In some embodiments, the backing 330 can be transparent (or substantially transparent), and the fluid management article 330 can be non-transparent. As a result, in some embodiments, the fluid management article 330 can include one or more openings or windows 345 configured to be positioned over a target (e.g., an insertion site), such that the target can be visualized while the medical dressing 300 is coupled to the skin and positioned over the target. In such embodiments, the backing 310 can overlap the opening 345 and the target, providing protection to the target, and also potentially coming into direct contact with the skin (e.g., such that the backing adhesive 316 directly contacts the skin). As a result, in some embodiments, it can be beneficial for the backing adhesive 316 to be a skin-contact adhesive and/or to be patterned (e.g., pattern coated), as shown in FIG. 3. Such patterning can facilitate fluid movement from the target site toward the edges of the opening 345 in the fluid management article 330 to be wicked and/or evaporated away from the target.

In some embodiments, as shown in FIG. 3, the opening 345 can be positioned toward one end of the dressing 300, e.g., toward a distal end of the dressing 300. In some embodiments, however, the opening 345 can be centered with respect to the dressing 300. Other configurations and arrangements of one or more openings 345 can also be employed.

Examples of medical articles that can be employed with the IV medical dressing 300 can include, but are not limited to, connector fittings, catheter systems (e.g., including catheters, catheter hubs, catheter adaptors, etc.), fluid supply lines, inserted ports, other similar articles, or combinations thereof. Examples of catheter systems can include, but are not limited to, intravenous (IV) catheters (e.g., peripheral intravenous catheters PIVs), central venous catheters (CVCs), peripherally inserted central catheters (PICCs), arterial catheters, urinary catheters, and dialysis catheters.

While not shown in FIG. 3, as described above with respect to FIGS. 1 and 2, the medical dressing 300 can further include one or more release liners positioned to cover any exposed adhesives prior to use. As a result of the opening 345 in the fluid management article 330, both the skin-contact adhesive 336 and the backing adhesive 316 (which may also be a suitable skin-contact adhesive) are exposed on an overall bottom or back surface of the medical dressing 300, and one or more release liners can be configured to cover both the skin-contact adhesive 336 and the backing adhesive 316.

As described above, the medical dressing 300 can further include any combination of tabs, frames or carrier layers to support the medical dressing, e.g., during handling and application.

Each embodiment shown in the figures is illustrated as a separate embodiment for clarity in illustrating a variety of features of the medical dressings of the present disclosure. However, it should be understood that any combination of elements and features of any of the embodiments illustrated in the figures and described herein can be employed in the medical dressings of the present disclosure. For example, an absorbent core is illustrated in the medical dressing 200 of FIG. 2; however, it should be understood that such an absorbent member can also be employed in the medical dressings 100 and 300 of FIGS. 1 and 3, respectively. In addition, the medical dressing 200 is illustrated as an island dressing, wherein the backing 210 extends beyond a periphery of the fluid management article 230. This island configuration can also be employed in the medical dressings 100 and 300 of FIGS. 1 and 3, respectively. Furthermore, the IV medical dressing 300 is illustrated as including the opening 345 in the fluid management article 330 to enhance visibility and visualization of a target site; however, openings in the fluid management articles 130 and 230 of FIGS. 1 and 2 can also be employed.

Methods of using medical dressings of the present disclosure, particularly for moving fluid away from a target site, are described in greater detail below.

Backings

Suitable backings for medical dressings of the present disclosure can include, but are not limited to, one or more of a fabric, a woven fibrous web, a nonwoven fibrous web, a knit, a polymeric film, other familiar dressing materials, or combinations thereof. In some embodiments, the backing materials can include transparent polymeric elastic films, and can include, but are not limited to, films formed of elastomeric polyurethanes, co-polyesters, polyethylenes, or combinations thereof. The backing can be a high moisture vapor permeable film. U.S. Pat. No. 3,645,835 describes methods of making such films and methods for testing their permeability.

The backings of the present disclosure advantageously should transmit moisture vapor at a rate equal to or greater than human skin. In some embodiments, the backing can be adhesive-coated (i.e., including the backing adhesive). In such embodiments, the adhesive-coated backing can transmit moisture vapor at a rate of at least 300 g/m$^2$/24 hrs/37° C./100-10% RH, and in some embodiments, at least 700 g/m$^2$/24 hrs/37° C./100-10% RH. The backing is generally conformable to anatomical surfaces. As such, when the backing is applied to an anatomical surface, it conforms to the surface even when the surface is moved. The backing can also be conformable to animal anatomical joints. When the joint is flexed and then returned to its unflexed position, the backing can be made such that it stretches to accommodate the flexion of the joint, but is resilient enough to continue to conform to the joint when the joint is returned to its unflexed condition.

The backing can be a flexible material. For example, the backing can be a film, paper, woven, knitted, or nonwoven material or a combination of one or more layers of film, paper, woven, knitted, or nonwoven. In some embodiments, it can be desirable that at least a portion of the backing is formed of a transparent material to allow for viewing of underlying skin, a medical device, and/or a target site.

By way of example only, in some embodiments, the backing can be formed of a film available under the trade designation TEGADERM® from 3M Company, St. Paul, Minn. In some embodiments, the backing can be formed of a compression dressing available under the trade designation COBAN® from 3M Company.

Fluid Management Articles

The fluid management article of the present disclosure is sometimes referred to herein as simply an "article" or a "porous article," or a "particle loaded fibrous web."

The article comprises a) porous polymeric particles and b) a fibrous porous matrix (or "fibrous substrate"), wherein the porous polymeric particles are distributed throughout the fibrous porous matrix. The porous polymeric particles include a polymerized product of a reaction mixture that contains i) a monomer composition and ii) a polypropylene glycol) having a weight average molecular weight of at least 500 grams/mole. The monomer composition contains at least 10 weight percent of a first monomer of Formula (I)

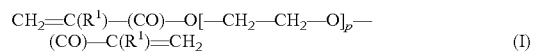
$$CH_2=C(R^1)-(CO)-O[-CH_2-CH_2-O]_p-\\(CO)-C(R^1)=CH_2 \quad (I)$$

based on a total weight of the monomer composition. In Formula (I), the variable p is an integer equal to at least 1 and $R^1$ is hydrogen or alkyl.

The variable p in Formula (I) is an integer no greater than 30, no greater than 20, no greater than 16, no greater than 12, or no greater than 10. The number average molecular weight of the ethylene oxide portion of the monomer (i.e., the group $-[CH_2CH_2-O]_p-$) is often no greater than 1200 grams/mole, no greater 1000 grams/mole, no greater than 800 grams/mole, no greater than 1000 grams, mole, no greater than 600 grams/mole, no greater than 400 grams/mole, no greater than 200 grams/mole, or no greater than 100 grams/mole. The group $R^1$ in Formula (I) is hydrogen or methyl.

Suitable first monomers of Formula (I) are commercially available from Sartomer (Exton, Pa., USA) under the trade designation SR206 for ethylene glycol dimethacrylate, SR231 for diethylene glycol dimethacrylate, SR205 for triethylene glycol dimethacrylate, SR210 and SR210A for polyethylene glycol dimethacrylate, SR259 for polyethylene glycol (200) diacrylate, SR603 and SR344 for polyethylene glycol (400) di(meth)acrylate, SR252 and SR610 for polyethylene glycol (600) di(meth)acrylate, and SR740 for polyethylene glycol (1000) dimethacrylate.

The reaction mixture used to form the porous polymeric particles also includes a poly(propylene glycol) having a weight average molecular weight of at least 500 grams/mole. The polypropylene glycol functions as a porogen that gets partially entrained within the polymerized product as it forms from the monomer composition. Because the polypropylene glycol has no polymerizable group, this material can be removed after formation of the polymerized product. Pores (i.e., void volume or free volume) are created when the previously entrained polypropylene glycol is removed. The polymeric particles resulting from the removal of the entrained polypropylene glycol are porous. In certain embodiments, at least some of these porous polymeric particles can have hollow centers, and thus be in the form of hollow beads. The presence of pores or the presence of both pores and hollow centers make the polymeric particles well suited for absorbing and wicking fluids, as well as holding active agents.

As mentioned above, the poly(propylene glycol) is removed from the polymerized product to provide the porous particles. In some embodiments, the resulting porous particles are "substantially free" of poly(propylene glycol). As used herein with reference to the poly(propylene glycol), the phrase "substantially free" means that no poly(propylene glycol), or only trace amounts of poly(propylene glycol) remain in the resulting particles. In some embodiments, "substantially free" of poly(propylene glycol) means that poly(propylene glycol) is present in the porous particles in an amount of no greater than 1 wt %; in some embodiments, no greater than 0.5 wt %; in some embodiments, no greater than 0.1 wt %; in some embodiments, no greater than 0.05 wt %; and in some embodiments, no greater than 0.01 wt %.

Any suitable molecular weight of poly(propylene glycol) can be used as the porogen. The molecular weight can affect the size of the pores that are formed in the polymeric particles. That is, the pore size tends to increase with the molecular weight of the poly(propylene glycol). The weight average molecular weight ($M_w$) is often at least 500 grams/mole, at least 800 grams/mole, or at least 1000 grams/mole. In some embodiments, the weight average molecular weight of the poly(propylene glycol) can be up to 10,000 gram/mole or greater. For ease of use, a poly(propylene glycol) that is a liquid at room temperature is often selected. Poly(propylene glycol) having a weight average molecular weight up to about 4000 grams/mole or 5000 grams/mole tends to be a liquid at room temperature. Poly(propylene glycol) that is not a liquid at room temperature can be used if it is initially dissolved in a suitable organic solvent such as an alcohol (for example, ethanol, n-propanol, or iso-propanol). The weight average molecular weight of the poly(propylene glycol) is often in a range of 500 to 10,000 grams/mole, in a range of 1000 to 10,000 grams/mole, in a range of 1000 to 8000 grams/mole, in a range of 1000 to 5000 grams/mole, in a range of 1000 to 4000 grams/mole.

In many embodiments of the first aspect, the reaction mixture used to form the porous polymeric particles includes (a) a first phase and (b) a second phase dispersed in the first phase, wherein a volume of the first phase is greater than a volume of the second phase. The first phase contains (i) a compound of Formula (II)

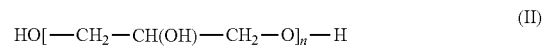

where the variable n is an integer equal to at least 1, and (ii) a nonionic surfactant. The second phase contains (i) a monomer composition comprising the monomer of Formula (I) as described above and (ii) a poly(propylene glycol) having a weight average molecular weight of at least 500 grams/mole.

The second phase of the reaction mixture is dispersed in the first phase of the reaction mixture and the volume of the first phase is greater than the volume of the second phase. That is, the first phase can be considered to be the continuous phase and the second phase can be considered to be the dispersed phase within the continuous phase. The first phase provides a non-polymerizable medium for suspending the second phase as droplets within the reaction mixture. The second phase droplets include i) a monomer composition that can undergo polymerization and ii) a porogen, which is poly(propylene glycol) having a weight average molecular weight of at least 500 grams/mole. The monomer of Formula (I) in the second phase is typically not miscible with the first phase.

The first phase of the reaction mixture includes (i) the compound of Formula (II) and (ii) a nonionic surfactant. The first phase is typically formulated to provide a suitable viscosity and volume for dispersion of the second phase as droplets within the first phase. If the viscosity of the first phase is too high, it can be difficult to provide the requisite shear to disperse the second phase. If the viscosity is too low, however, it can be difficult to suspend the second phase and/or to form polymeric particles that are relatively uniform and well separated from each other.

Suitable compounds of Formula (II) typically have a value of n that is in a range of 1 to 20, in a range of 1 to 16, in a range of 1 to 12, in a range of 1 to 10, in a range of 1 to 6, or in a range of 1 to 4. In many embodiments, the compound of Formula (II) is glycerol where the variable n is equal to 1. Other example compounds of Formula (II) are diglycerol (n is equal to 2), polyglycerol-3 (n is equal to 3), polyglycerol-4 (n is equal to 4), or polyglycerol-6 (n is equal to 6). The polyglycerols, which can be referred to as polyglycerins, are often a mixture of materials with varying molecular weight (i.e., materials with different values for n). Polyglycerols, diglycerol, and glycerol are commercially available, for example, from Solvay Chemical (Brussels, Belgium) and Wilshire Technologies (Princeton, N.J., USA).

In addition to the compound of Formula (II), the first phase includes a nonionic surfactant. The nonionic surfactant increases the porosity on the surface of the final polymeric particles. The first phase is typically free or substantially free of an ionic surfactant that could interfere with the polymerization reaction of the monomers within the second phase. As used herein with reference to the ionic surfactant, the phrase "substantially free" means that no ionic surfactant is purposefully added to the first phase but may be present as a trace impurity in one of the other components in the first phase. Any impurity is typically present in an amount no greater than 0.5 weight percent, no greater than 0.1 weight percent, or no greater than 0.05 weight percent, or no greater than 0.01 weight percent based on a total weight of the first phase.

Any suitable nonionic surfactant can be used in the first phase. The nonionic surfactant often has hydroxyl group or ether linkages (for example, —$CH_2$—O—$CH_2$—) in one portion of the molecule that can hydrogen bond with other components of the reaction mixture. Suitable nonionic surfactants include, but are not limited to, alkyl glucosides, alkyl glucamides, alkyl polyglucosides, polyethylene glycol alkyl ethers, block copolymers of polyethylene glycol and polypropylene glycol, and polysorbates. Examples of suitable alkyl glucosides include, but are not limited to, octyl glucoside (also referred to as octyl-beta-D-glucopyranoside) and decyl glucoside (also referred to as decyl-beta-D-glucopyranoside). Examples of suitable alkyl glucamides include, but are not limited to, octanoyl-N-methylglucamide, nonanoyl-N-methylglucamide, and decanoyl-N-methylglucamide. These surfactants can be obtained, for example, from Sigma Aldrich (St. Louis, Mo., USA) or Spectrum Chemicals (New Brunswick, N.J., USA). Examples of suitable alkyl polyglucosides include, but are not limited to, those commercially available from Cognis Corporation (Monheim, Germany) under the trade designation APG (for example, APG 325) and those commercially available from Dow Chemical (Midland, Mich., USA) under the trade designation TRITON (for example, TRITON BG-10 and TRITON CG-110). Examples of polyethylene glycol alkyl ethers include, but are not limited to, those commercially available under the trade designation BRIJ (for example, BRIJ 58 and BRIJ 98) from Sigma Aldrich (St. Louis, Mo., USA). Examples of block copolymers of polyethylene glycol and polypropylene glycol include, but are not limited to, those commercially available under the trade designation PLURONIC from BASF (Florham Park, N.J., USA). Examples of polysorbates include, but are not limited to, those commercially available under the trade designation TWEEN from ICI American, Inc. (Wilmington, Del., USA).

The nonionic surfactant can be present in the first phase in any suitable amount. Often, the surfactant is present in an amount equal to at least 0.5 weight percent, at least 1 weight percent, or at least 2 weight percent based on a total weight of the first phase. The surfactant can be present in an amount up to 15 weight percent, up to 12 weight percent, or up to 10 weight percent based on a total weight of the first phase. For example, the surfactant is often present in the first phase in an amount in a range of 0.5 to 15 weight percent, in a range of 1 to 12 weight percent, in a range of 0.5 to 10 weight percent, or in a range of 1 to 10 weight percent based on the total weight of the first phase.

Optionally, water or an organic solvent that is miscible with the compound of Formula (II) can be present in the first reaction mixture. Suitable organic solvents include, for example, an alcohol such as methanol, ethanol, n-propanol, or isopropanol. The amount of any optional water or organic solvent is selected so that the desired viscosity of the first phase can be achieved. The amounts of the optional water or organic solvent is often no greater than 10 weight percent, no greater than 5 weight percent, or no greater than 1 weight percent based on the total weight of the first phase. If higher amounts of water are included, the porosity may decrease. In some embodiments, the first phase is free or substantially free of the optional water or organic solvent. As used herein with reference to the optional water or organic solvent, the term "substantially free" means that water or organic solvent is not purposely added to the first phase but may be present as an impurity in one of the other components in the first phase. For example, the amount of the optional water or organic solvent is less than 1 percent, less than 0.5 weight percent, or less than 0.1 weight percent based on a total weight of the first phase.

The reaction mixture includes a second phase dispersed in the first phase. The second phase includes both i) a monomer composition and ii) a polypropylene glycol) having a weight average molecular weight of at least 500 grams/mole. The monomer composition is polymerized in the second phase to from the polymeric particles. The polypropylene glycol functions as a porogen that gets partially entrained within the polymerized product as it is formed from the monomer composition.

The volume of the first phase is greater than the volume of the second phase. The volume of the first phase is sufficiently large compared to the volume of the second phase so that the second phase can be dispersed in the form of droplets within the first phase. Within each droplet, the monomer composition is polymerized to form a polymerized product. To form particles from the second phase, the volume ratio of the first phase to the second phase is typically at least 2:1. As the volume ratio increases (for example, when the ratio is at least 3:1, at least 4:1, or at least 5:1), beads can be formed that have a relatively uniform size and shape. If the volume ratio is too large, however, the reaction efficiency is diminished (i.e., a smaller amount of polymeric particles is produced). The volume ratio is generally no greater than 25:1, no greater than 20:1, no greater than 15:1, or no greater than 10:1.

In some embodiments, the first monomer of Formula (I) as described above is the only monomer in the monomer composition of the second phase. In other embodiments, the first monomer of Formula (I) can be used in combination with at least one second monomer. The second monomer has a single free radically polymerizable group such as an ethylenically unsaturated group, which is often a (meth) acryloyl group of formula $H_2C=CR^1-(CO)-$ where $R^1$ is hydrogen or methyl. Suitable second monomers are not miscible with the first phase but can be miscible or not miscible with the first monomer of Formula (I). The second monomer is often added to alter the hydrophobicity or hydrophilicity of the porous polymeric material. The addition of these monomers can, however, diminish the porosity of the polymeric particles and/or increase the size of the polymeric particles.

Some example second monomers are of Formula (III).

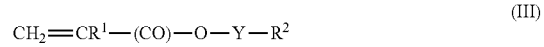

$$CH_2=CR^1-(CO)-O-Y-R^2 \qquad (III)$$

In this formula, group $R^1$ is hydrogen or methyl. In many embodiments, $R^1$ is hydrogen. Group Y is a single bond, alkylene, oxyalkylene, or poly(oxyalkylene). Group $R^2$ is a carbocyclic group or heterocyclic group. These second monomers tend to be miscible with the first monomer of Formula (I) in the second phase but are not miscible with the first phase.

As used herein, the term "alkylene" refers to a divalent group that is a radical of an alkane and includes groups that are linear, branched, cyclic, bicyclic, or a combination thereof. As used herein, the term "oxyalkylene" refers to a divalent group that is an oxy group bonded directly to an alkylene group. As used herein, the term "poly(oxyalkylene)" refers to a divalent group having multiple oxyalkylene groups. Suitable Y alkylene and oxyalkylene groups typically have 1 to 20 carbon atoms, 1 to 16 carbon atoms, 1 to 12 carbon atoms, 1 to 10 carbon atoms, 1 to 8 carbon atoms, 1 to 6 carbon atoms, or 1 to 3 carbon atoms. The oxyalkylene is often oxyethylene or oxypropylene. Suitable poly(oxyalkylene) groups typically have 2 to 20 carbon atoms, 2 to 16 carbon atoms, 2 to 12 carbon atoms, 2 to 10 carbon atoms, 2 to 8 carbon atoms, 2 to 6 carbon atoms, or 2 to 4 carbon atoms. The poly(oxyalkylene) is often poly(oxyethylene), which can be referred to as poly(ethylene oxide) or poly(ethylene glycol).

Carbocyclic $R^2$ groups can have a single ring or can have multiple rings such as fused rings or bicyclic rings. Each ring can be saturated, partially unsaturated, or unsaturated. Each ring carbon atom can be unsubstituted or substituted with alkyl groups. Carbocyclic groups often have 5 to 12 carbon atoms, 5 to 10 carbon atoms, or 6 to 10 carbon atoms. Examples of carbocyclic groups include, but are not limited to, phenyl, cyclohexyl, cyclopentyl, isobornyl, and the like. Any of these carbocyclic groups can be substituted with an alkyl group having 1 to 20 carbon atoms, 1 to 10 carbon atoms, 1 to 6 carbon atoms, or 1 to 4 carbon atoms.

Heterocyclic $R^2$ groups can have a single ring or multiple rings such as fused rings or bicyclic rings. Each ring can be saturated, partially unsaturated, or unsaturated. The heterocyclic group contains at least one heteroatom selected from oxygen, nitrogen, or sulfur. The heterocyclic group often has 3 to 10 carbon atoms and 1 to 3 heteroatoms, 3 to 6 carbon atoms and 1 to 2 heteroatoms, or 3 to 5 carbon atoms and 1 to 2 heteroatoms. Examples of heterocyclic rings include, but are not limited to, tetrahydrofurfuryl.

Exemplary monomers of Formula (III) for use as the second monomer include, but are not limited to, benzyl (meth)acrylate, 2-phenoxyethyl (meth)acrylate (commercially available from Sartomer under the trade designation SR339 and SR340), isobornyl (meth)acrylate, tetrahydrofurfuryl (meth)acrylate (commercially available from Sartomer under the trade designation SR285 and SR203), 3,3,5-trimethylcyclohexyl (meth)acrylate (commercially available from Sartomer under the trade designation CD421 and CD421A), and ethoxylated nonyl phenol acrylate (commercially available from Sartomer under then trade designation SR504, CD613, and CD612).

Other example second monomers are alkyl (meth)acrylates of Formula (IV).

$$CH_2 = CR^1 - (CO) - O - R^3 \quad (IV)$$

In Formula (IV), group $R^1$ is hydrogen or methyl. In many embodiments, $R^1$ is hydrogen. Group $R^3$ is a linear or branched alkyl having 1 to 20 carbon atoms, 1 to 10 carbon atoms, 1 to 6 carbon atoms, or 1 to 4 carbon atoms. These second monomers tend to be miscible with the first monomer of Formula (I) in the second phase but are not miscible with the first phase.

Examples of alkyl (meth)acrylates of Formula (IV) include, but are not limited to, methyl (meth)acrylate, ethyl (meth)acrylate, n-propyl (meth)acrylate, isopropyl (meth)acrylate, n-butyl (meth)acrylate, isobutyl (meth)acrylate, n-pentyl (meth)acrylate, 2-methylbutyl (meth)acrylate, n-hexyl (meth)acrylate, 4-methyl-2-pentyl (meth)acrylate, 2-ethylhexyl (meth)acrylate, 2-methylhexyl (meth)acrylate, n-octyl (meth)acrylate, isooctyl (meth)acrylate, 2-octyl (meth)acrylate, isononyl (meth)acrylate, isoamyl (meth)acrylate, n-decyl (meth)acrylate, isodecyl (meth)acrylate, 2-propylheptyl (meth)acrylate, isotridecyl (meth)acrylate, isostearyl (meth)acrylate, octadecyl (meth)acrylate, 2-octyldecyl (meth)acrylate, dodecyl (meth)acrylate, lauryl (meth)acrylate, and heptadecanyl (meth)acrylate.

In some embodiments, the only monomers in the monomer composition are the first monomer of Formula (I) and the second monomer of Formula (III), Formula (IV), or both. Any suitable amounts of the first monomer and second monomer can be used provided that the monomer composition contains at least 10 weight percent of the first monomer of Formula (I). The addition of a second monomer of Formula (III), Formula (IV), or both tends to increase the hydrophobicity of the porous polymeric particles. The monomer composition often contains 10 to 90 weight percent of the first monomer and 10 to 90 weight percent of the second monomer based on a total weight of monomers in the monomer composition. For example, the second phase can contain 20 to 80 weight percent of the first monomer and 20 to 80 weight percent of the second monomer, 25 to 75 weight percent of the first monomer and 25 to 75 weight percent of the second monomer, 30 to 70 weight percent of the first monomer and 30 to 70 weight percent of the second monomer, or 40 to 60 weight percent of the first monomer and 40 to 60 weight percent of the second monomer based on a total weight of monomers in the monomer composition.

Depending on the final use of the polymeric particles prepared, it can be desirable to include at least one hydrophilic second monomer in the monomer composition. The addition of a hydrophilic second monomer tends to make the polymeric particles more suitable for applications where the particles will be exposed to aqueous-based materials such as aqueous-based samples. Additionally, the use of a hydrophilic second monomer allows the porous polymeric particles to be dispersed in water more easily during the preparation of the porous article using, for example, a wetlaid process. Hydrophilic second monomers are selected so that they are not miscible with the first phase. These monomers may or may not be miscible with the first monomer of Formula (I).

Some example hydrophilic second monomers are hydroxyl-containing monomers of Formula (V).

$$CH_2 = CR^1 - (CO) - O - R^4 \quad (V)$$

In Formula (V), group $R^1$ is hydrogen or methyl. In many embodiments, $R^1$ is hydrogen. Group $R^4$ is an alkyl substituted with one or more hydroxyl groups or a group of formula $-(CH_2CH_2O)_qCH_2CH_2OH$ where q is an integer equal to at least 1. The alkyl group typically has 1 to 10 carbon atoms, 1 to 6 carbon atoms, 1 to 4 carbon atoms, or 1 to 3 carbon atoms. The number of hydroxyl groups is often in a range of 1 to 3. The variable q is often in a range of 1 to 20, in a range of 1 to 15, in a range of 1 to 10, or in a range of 1 to 5. In many embodiments, the second monomer of Formula (IV) has a single hydroxyl group.

Example monomers of Formula (V) include, but are not limited to, 2-hydroxyethyl (meth)acrylate, 2-hydroxypropyl (meth)acrylate, 3-hydroxypropyl (meth)acrylate, and 4-hydroxybutyl (meth)acrylate), 2-hydroxylbutyl (meth)acrylate, polyethylene glycol mono(meth)acrylate (for example, monomers commercially available from Sartomer (Exton, Pa., USA) under the trade designation CD570, CD571, and CD572), and glycol mono(meth)acrylate.

Other example hydrophilic second monomers are hydroxyl-containing monomers of Formula (VI).

$$CH_2 = CR^1 - (CO) - O - R^5 - O - Ar \quad (VI)$$

In Formula (VI), group $R^1$ is hydrogen or methyl. In many embodiments, $R^1$ is hydrogen. Groups $R^5$ is an alkylene substituted with at least one hydroxyl group. Suitable alkylene groups often have 1 to 10 carbon atoms, 1 to 6 carbon atoms or 1 to 4 carbon atoms. The alkylene group $R^5$ can be substituted with 1 to 3 hydroxyl groups but is often substituted with a single hydroxyl group. The group Ar is an aryl group having 6 to 10 carbon atoms. In many embodiments, the Ar group is phenyl. One example monomer of Formula (VI) is 2-hydroxy-2-phenoxypropyl (meth)acrylate.

If the second monomer is of Formula (V) or (VI), which are hydroxyl-containing monomers, the amount of this monomer that can be combined with the first monomer of Formula (I) is often no greater than 2 weight percent based on a total weight of monomers in the monomer composition. If greater than about 2 weight percent of the second monomer of Formula (V) or (VI) is used, the resulting polymeric particles tend to have diminished porosity.

Other hydrophilic monomers can be used as the second monomers in larger quantities than the second monomers of Formula (V) or (VI) without diminishing the porosity of the resulting polymeric particles. For example, sulfonic acid-containing monomers of Formula (VII) can be included in the monomer composition along with the first monomer of Formula (II) or a salt thereof.

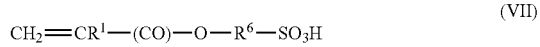

(VII)

In Formula (VII), group $R^1$ is hydrogen or methyl. In many embodiments, $R^1$ is hydrogen. Group $R^6$ is an alkylene having 1 to 10 carbon atoms, 1 to 6 carbon atoms, or 1 to 4 carbon atoms. Examples of sulfonic acid-containing monomers of Formula (VII) include, but are not limited to, sulfoethyl (meth)acrylate and sulfopropyl (meth)acrylate. Depending on the pH conditions, these second monomers can impart an ionic (for example, anionic) character to the porous polymeric particles. The counter ion is often a cation of such as an alkali metal ion, an alkaline earth metal ion, an ammonium ion, or an alkyl substituted ammonium ions such as tetraalkyl ammonium ion.

If the second monomer is a sulfonic acid-containing monomer of Formula (VII), the monomer composition can contain up to 20 weight percent of this monomer based on a total weight of monomers in the monomer composition. In some embodiments, the only monomers in the monomer composition are the first monomer of Formula (I) and the second monomer of Formula (VII). The monomer composition often contains 80 to 99 weight percent of the first monomer of Formula (I) and 1 to 20 weight percent of the second monomer of Formula (VII) based on a total weight of monomers in the monomer composition. For example, the monomer composition can contain 85 to 99 weight percent of the first monomer and 1 to 15 weight percent of the second monomer, 90 to 99 weight percent of the first monomer and 1 to 10 weight percent of the second monomer, and 95 to 99 weight percent of the first monomer and 1 to 5 weight percent of the second monomer based on a total weight of monomers in the monomer composition.

In other embodiments, the monomer composition includes a first monomer of Formula (I) and two second monomers. The two second monomers are a sulfonic acid-containing monomer, such as those of Formula (VII), and a hydroxyl-containing monomer, such as those of Formula (V) or (VI). When the hydroxyl-containing monomer is combined with a sulfonic acid-containing monomer, higher amounts of the hydroxyl-containing monomer can be added to the monomer composition without substantially decreasing the porosity of the resulting polymeric particles. That is, the amount of the hydroxyl-containing monomer can be greater than 2 weight percent based on the weight of the monomers in the monomer composition. The monomer composition often contains 80 to 99 weight percent of the first monomer of Formula (II) and 1 to 20 weight percent of the second monomer, wherein the second monomer is a mixture of the sulfonic acid-containing monomer and the hydroxyl-containing monomer. Up to 50 weight percent, up to 40 weight percent, up to 20 weight percent, or up to 10 weight percent of the second monomer can be the hydroxyl-containing monomer.

Other second monomers that can impart an ionic (for example, anionic) character to the porous polymeric particles have a carboxylic acid group (—COOH). Examples of such monomers include, but are not limited to, (meth)acrylic acid, maleic acid, and β-carboxyethyl acrylate. If a monomer having a carboxylic acid group is added, this monomer typically is present in an amount no greater than 20 weight percent, no greater than 15 weight percent, no greater than 10 weight percent, or no greater than 5 weight percent based on the total weight of monomers in the monomer composition. For example, the monomer composition often contains 80 to 99 weight percent of the first monomer of Formula (I) and 1 to 20 weight percent of the second monomer having a carboxylic acid group. For example, the monomer composition can contain 85 to 99 weight percent of the first monomer and 1 to 15 weight percent of the second monomer, 90 to 99 weight percent of the first monomer and 1 to 10 weight percent of the second monomer, and 95 to 99 weight percent of the first monomer and 1 to 5 weight percent of the second monomer based on a total weight of monomers in the monomer composition.

Still other hydrophilic monomers are those of Formula (VIII)

(VIII)

having a quaternary ammonium group. The group $R^7$ is an alkylene having 1 to 10 carbon atoms, 1 to 6 carbon atoms, or 1 to 4 carbon atoms. The group $R^8$ is an alkyl having 1 to 4 carbon atoms or 1 to 3 carbon atoms. The anion $X^-$ can be any anion but is often a halide such as chloride. Alternatively the anion can be a sulfate and be associated with two ammonium-containing cationic monomers.

Examples include, but are not limited to, (meth)acrylamidoalkyltrimethylammonium salts (for example, 3-methacrylamidopropyltrimethylammonium chloride and 3-acrylamidopropyltrimethylammonium chloride) and (meth)acryloxyalkyltrimethylammonium salts (for example, 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate). Depending on the pH conditions, these third monomers can impart an ionic (for example, cationic) character to the porous polymeric particles.

If a second monomer of Formula (VIII) is added, this monomer typically is present in an amount no greater than 20 weight percent, no greater than 15 weight percent, no greater than 10 weight percent, or no greater than 5 weight percent based on the total weight of monomers in the monomer composition. For example, the monomer composition often contains 80 to 99 weight percent of the first monomer of Formula (I) and 1 to 20 weight percent of the second monomer of Formula (VIII). For example, the monomer composition can contain 85 to 99 weight percent of the first monomer and 1 to 15 weight percent of the second monomer, 90 to 99 weight percent of the first monomer and 1 to 10 weight percent of the second monomer, and 95 to 99 weight percent of the first monomer and 1 to 5 weight percent of the second monomer based on a total weight of monomers in the monomer composition.

Often if an ionic monomer is added such as one having a carboxylic acid group or a salt thereof, a sulfonic acid group or a salt thereof (such as of Formula (VII)), or an ammonia group (such as of Formula (VIII)), the ionic monomer is often present in low amounts such as in a range of 1 to 10 weight percent, in a range of 1 to 5 weight percent, or in a range of 1 to 3 percent based on the total weight of monomers in the monomer composition. Particularly when the preparation of porous polymeric particles having an average diameter less than about 10 micrometers, less than about 5 micrometers, less than about 4 micrometers, or less than about 3 micrometers are desired, lower concentrations of the ionic monomers in the monomer composition may be preferred. For use with hydrophobic materials or nonionic materials, it may be preferable to have monomer compositions that are free or substantially free of ionic monomers. As used herein in reference to the amount of ionic monomers, "substantially free" means that no such monomer is intentionally added or is added at an amount no greater than 1 weight percent, no greater than 0.5 weight percent, no greater than 0.2 weight percent, or no greater than 0.1 weight percent based on the total weight of monomers in the monomer composition.

In some embodiments, it is preferable that the monomer composition contains only a monomer of Formula (I) or a mixture of a first monomer of Formula (I) and a second monomer of Formula (III) added to increase the hydrophobicity of the porous polymeric particles. For example, some monomer compositions often contains 10 to 90 weight percent of the first monomer and 10 to 90 weight percent of the second monomer based on a total weight of monomers in the monomer composition. For example, the monomer composition can contain 20 to 80 weight percent of the first monomer and 20 to 80 weight percent of the second monomer, 25 to 75 weight percent of the first monomer and 25 to 75 weight percent of the second monomer, 30 to 70 weight percent of the first monomer and 30 to 70 weight percent of the second monomer, or 40 to 60 weight percent of the first monomer and 40 to 60 weight percent of the second monomer.

The monomer composition can optionally contain a third monomer with at least two polymerizable groups. The polymerizable groups are typically (meth)acryloyl groups. In many embodiments, the third monomer has two or three (meth)acryloyl groups. The third monomer typically is not miscible with the first phase and may or may not be miscible with the first monomer of Formula (I).

Some third monomers have a hydroxyl group. Such monomers can function as crosslinkers like the first monomer of Formula (I) but can provide polymeric particles with increased hydrophilic character. An example hydroxyl-containing third monomer is glycerol di(meth)acrylate.

Some third monomers are selected to have at least three polymerizable groups. Such third monomers can be added to provide more rigidity to the resulting polymeric particles. The addition of these third monomers tends to minimize swelling of the polymeric particles when exposed to water. Suitable third monomers include, but are not limited to, ethoxylated trimethylolpropane tri(meth)acrylates such as ethoxylated (15) trimethylolpropane triacrylate (commercially available under the trade designation SR9035 from Sartomer) and ethoxylated (20) trimethylolpropane triacrylate (commercially available under the trade designation SR415 from Sartomer); propoxylated trimethylolpropane tri(meth)acrylates such as propoxylated (3) trimethylolpropane triacrylate (commercially available under the trade designation SR492 from Sartomer) and propoxylated (6) trimethylolpropane triacrylate (commercially available under the trade designation CD501 from Sartomer); tris(2-hydroxyethyl) isocyanurate tri(meth)acrylates such as tris (2-hydroxyethyl) isocyanurate triacrylate (commercially available under the trade designations SR368 and SR368D from Sartomer); and propoxylated glyceryl tri(meth)acrylates such as propoxylated (3) glycerol triacrylate (commercially available under the trade designation SR9020 and SR9020HP from Sartomer).

When a third monomer is present in the monomer composition, any suitable amount can be used. The third monomer is often used in an amount up to 20 weight percent based on the total weight of monomers in the monomer composition. In some embodiments, the amount of the third monomer is up to 15 weight percent, up to 10 weight percent, or up to 5 weight percent.

In some embodiments, the monomer composition contains at least 10 weight percent, at least 20 weight percent, at least 30 weight percent, at least 35 weight percent, at least 40 weight percent, at last 45 weight percent, at least 50 weight percent, at least 55 weight percent, at least 60 weight percent, at least 65 weight percent, at least 70 weight percent, at least 75 weight percent at least 80 weight percent, at least 90 weight percent, or at least 95 weight percent of the first monomer of Formula (I). The remaining amount of the monomer composition can include any combination of the second and third monomers described above. In some embodiments, any remaining amount is a monomer of Formula (III).

The monomer composition often contains 10 to 100 weight percent of the first monomer, 0 to 90 weight percent of the second monomer, and 0 to 20 weight percent of the third monomer based on a total weight of monomers in the monomer composition. For example, the monomer composition can contain 10 to 90 weight percent of the first monomer, 10 to 90 weight percent of the second monomer, and 0 to 20 weight percent of the third monomer. The monomer composition can contain 10 to 89 weight percent of the first monomer, 10 to 89 weight percent of the second monomer, and 1 to 20 weight percent of the third monomer based on a total weight of the monomer composition.

In addition to the monomer composition, the second phase contains poly(propylene glycol), which functions as a porogen. The poly(propylene glycol) is soluble in the monomer composition within the second phase but is dispersible within the first phase. Stated differently, the poly(propylene glycol) is completely miscible with the second phase and partially miscible with the first phase. The poly(propylene glycol) is removed after polymerization of the monomer composition to provide pores (for example, void volumes or free volumes) in the polymeric particle. The poly(propylene glycol) does not have any polymerizable groups (i.e., it is not a monomer) and, in general, is not covalently attached to the polymeric particles that forms within the second phase.

It is believed that some of the poly(propylene glycol) become entrained within the polymerized product. It is further believed that some of the poly(propylene glycol) is positioned on the interface between the first phase and the second phase as the polymerized product is formed in the second phase. The presence of the poly(propylene glycol) at the surface of the forming polymerized product results in the formation of a polymeric particle having surface porosity. The surface porosity can be seen from electron micrographs of the polymeric particles such as in FIG. 4.

The second phase can contain up to 50 weight percent poly(propylene glycol). If higher amounts of the poly(propylene glycol) are used, there may be an insufficient amount of the monomer composition included in the second phase to form polymeric particles that are uniformly shaped. In many embodiments, the second phase can contain up to 45 weight percent, up to 40 weight percent, up to 35 weight percent, up to 30 weight percent, or up to 25 weight percent poly(propylene glycol) based on a total weight of the second phase. The second phase typically contains at least 5 weight percent poly(propylene glycol). If lower amounts of the poly(propylene glycol) are used, the porosity of the resulting polymeric particles may be insufficient. The second phase typically can contain at least 10 weight percent, at least 15 weight percent, or at least 20 weight percent poly(propylene glycol). In some embodiments, the second phase contains 5 to 50 weight percent, 10 to 50 weight percent, 10 to 40 weight percent, 10 to 30 weight percent, 20 to 50 weight percent, 20 to 40 weight percent, or 25 to 35 weight percent poly(propylene glycol) based on the total weight of the second phase.

In some embodiments, the second phase contains 50 to 90 weight percent monomer composition and 10 to 50 weight percent poly(propylene glycol), 60 to 90 weight percent monomer composition and 10 to 40 weight percent poly(propylene glycol), 50 to 80 weight percent monomer composition and 20 to 50 weight percent poly(propylene glycol), or 60 to 80 weight percent monomer composition and 20 to 40 weight percent poly(propylene glycol) based on a total weight of the second phase.

In addition to the monomer composition and poly(propylene glycol), the second phase often contains an initiator for free radical polymerization of the monomer composition. Any suitable initiator known in the art can be used. The initiator can be a thermal initiator, a photoinitiator, or both. The specific initiator used is often selected based on its solubility in the second phase. The initiator is often used at a concentration of 0.1 to 5 weight percent, 0.1 to 3 weight percent, 0.1 to 2 weight percent, or 0.1 to 1 weight percent based on the weight of monomers in the monomer composition.

When a thermal initiator is added to the reaction mixture, polymeric particles can be formed at room temperature (i.e., 20 to 25 degrees Celsius) or at an elevated temperature. The temperature needed for polymerization often depends on the particular thermal initiator used. Examples of thermal initiators include organic peroxides and azo compounds.

When a photoinitiator is added to the reaction mixture, polymeric particles can be formed by the application of actinic radiation. Suitable actinic radiation includes electromagnetic radiation in the infrared region, visible region, ultraviolet region, or a combination thereof.

Examples of photoinitiators suitable in the ultraviolet region include, but are not limited to, benzoin, benzoin alkyl ethers (for example, benzoin methyl ether and substituted benzoin alkyl ethers such anisoin methyl ether), phenones (for example, substituted acetophenones such as 2,2-dimethoxy-2-phenylacetophenone and substituted alpha-ketols such as 2-methyl-2-hydroxypropiophenone), phosphine oxides, polymeric photoinitiators, and the like.

Commercially available photoinitiators include, but are not limited to, 2-hydroxy-2-methyl-1-phenyl-propane-1-one (for example, commercially available under the trade designation DAROCUR 1173 from Ciba Specialty Chemicals), a mixture of 2,4,6-trimethylbenzoyl-diphenyl-phosphine oxide and 2-hydroxy-2-methyl-1-phenyl-propan-1-one (for example, commercially available under the trade designation DAROCUR 4265 from Ciba Specialty Chemicals), 2,2-dimethoxy-1,2-diphenylethan-1-one (for example, commercially available under the trade designation IRGACURE 651 from Ciba Specialty Chemicals), a mixture of bis(2,6-dimethoxybenzoyl)-2,4,4-trimethyl-pentylphosphine oxide and 1-hydroxy-cyclohexyl-phenyl-ketone (for example, commercially available under the trade designation IRGACURE 1800 from Ciba Specialty Chemicals), a mixture of bis(2,6-dimethoxybenzoyl)-2,4,4-trimethyl-pentylphosphine oxide (for example, commercially available under the trade designation IRGACURE 1700 from Ciba Specialty Chemicals), 2-methyl-1[4-(methylthio)phenyl]-2-morpholinopropan-1-one (for example, commercially available under the trade designation IRGACURE 907 from Ciba Specialty Chemicals), 1-hydroxy-cyclohexyl-phenyl-ketone (for example, commercially available under the trade designation IRGACURE 184 from Ciba Specialty Chemicals), 2-benzyl-2-(dimethylamino)-1-[4-(4-morpholinyl)phenyl]-1-butanone (for example, commercially available under the trade designation IRGACURE 369 from Ciba Specialty Chemicals), bis(2,4,6-trimethylbenzoyl)-phenylphosphine oxide (for example, commercially available under the trade designation IRGACURE 819 from Ciba Specialty Chemicals), ethyl 2,4,6-trimethylbenzoyldiphenyl phosphinate (for example, commercially available from BASF, Charlotte, N.C. under the trade designation LUCIRIN TPO-L), and 2,4,6-trimethylbenzoyldiphenylphosphine oxide (for example, commercially available from BASF, Charlotte, N.C. under the trade designation LUCIRIN TPO).

The reaction mixture often includes at least 5 weight percent of the second phase (dispersed phase) and up to 95 weight percent of the first phase (continuous phase). In some embodiments, the reaction mixture contains 5 to 40 weight percent second phase and 60 to 95 weight percent first phase, 5 to 30 weight percent second phase and 70 to 95 weight percent first phase, 10 to 30 weight percent second phase and 70 to 90 weight percent first phase, or 5 to 20 weight percent second phase and 80 to 95 weight percent first phase. The weight percents are based on a total weight of the reaction mixture.

To prepare the polymeric particles or beads, droplets of the second phase are formed in the first phase. The components of the second phase are often mixed together prior to addition to the first phase. For example, the monomer composition, initiator, and the polypropylene glycol) can be blended together and then this blended composition, which is the second phase, can be added to the first phase. The resulting reaction mixture is often mixed under high shear to form a micro-emulsion. The size of the dispersed second phase droplets can be controlled by the amount of shear or the mixing rate. The size of the droplets can be determined by placing a sample of the mixture under an optical microscope prior to polymerization. Although any desired droplet size can be used, the average droplet diameter is often less than 200 micrometers, less than 100 micrometers, less than 50 micrometers, less than 25 micrometers, less than 10 micrometers, or less than 5 micrometers. For example, the average droplet diameter can be in the range of 1 to 200 micrometers, 1 to 100 micrometers, 5 to 100 micrometers, 5 to 50 micrometers, 5 to 25 micrometers, or 5 to 10 micrometers.

If a photoinitiator is used, the reaction mixture is often spread on a non-reactive surface at a thickness that can be penetrated by the desired actinic radiation. The reaction mixture is spread using methods that do not cause the droplets to coalesce. For example, the reaction mixture can be formed using an extrusion method. Often, the actinic radiation is in the ultraviolet region of the electromagnetic spectrum. If the ultraviolet radiation is applied from only the top surface of the reaction mixture layer, the thickness of the layer can be up to about 10 millimeters. If the reaction mixture layer is exposed to ultraviolet radiation from both the top and bottom surfaces, the thickness can be greater such as up to about 20 millimeters. The reaction mixture is subjected to the actinic radiation for a time sufficient to react the monomer composition and form polymeric particles. The reaction mixture layer is often polymerized within 5 minutes, within 10 minutes, within 20 minutes, within 30 minutes, within 45 minutes, or within 1 hour depending on the intensity of the actinic radiation source and the thickness of the reaction mixture layer.

If a thermal initiator is used, the droplets can be polymerized while continuing to mix the reaction mixture. Alternatively, the reaction mixture can be spread on a non-reactive surface to any desired thickness. The reaction mixture layer can be heated from the top surface, from the bottom surface, or both to form the polymeric particles. The thickness is often selected to be comparable to that use with the use of actinic radiation such as ultraviolet radiation.

In many embodiments, a photoinitiator is preferred over a thermal initiator because lower temperatures can be used for polymerization. That is, the use of actinic radiation such as ultraviolet radiation can be used to minimize degradation of various components of the reaction mixture that might be sensitive to temperatures needed for use with thermal initiators. Further, the temperatures typically associated with the use of thermal initiators may undesirably alter the solubility of the various components of the reaction mixture between the first phase and the dispersed second phase.

During the polymerization reaction, the monomer composition reacts within the second phase droplets suspended in the first phase. As polymerization progresses, the poly(propylene glycol) included in the second phase gets partially entrained within the polymerized product. Although it is possible that some portion of the poly(propylene glycol) can be covalently attached to the polymeric product through a chain transfer reaction, preferably the poly(propylene glycol) is not bonded to the polymeric product. The polymerized product is in the form of particles. In some embodiments, the particles are polymeric beads having a relatively uniform size and shape.

After formation of the polymerized product (i.e., polymeric particles containing entrained poly(propylene glycol)), the polymerized product can be separated from the first phase. Any suitable separation method can be used. For example, water is often added to lower the viscosity of the first phase. Particles of the polymerized product can be separated from the other components by decantation, filtration, or centrifugation. The particles of the polymerized product can be further washed by suspending them in water and collecting them a second time by decantation, filtration, or centrifugation.

The particles of the polymerized product can then be subjected to one or more washing steps to remove the poly(propylene glycol) porogen. Suitable solvents for removing the poly(propylene glycol) include, for example, acetone, methyl ethyl ketone, toluene, and alcohols such as ethanol, n-propanol, or iso-propanol. Stated differently, the entrained poly(propylene glycol) is removed from the polymerized product using solvent extraction methods. Pores are created where the poly(propylene glycol) previously resided.

In many embodiments, the resulting porous polymeric particles (the polymerized product after removal of the poly(propylene glycol) porogen) have an average diameter that is less than 200 micrometers, less than 100 micrometers, less than 50 micrometers, less than 25 micrometers, less than 10 micrometers, or less than 5 micrometers. For example, the porous polymeric particles can have an average diameter in the range of 1 to 200 micrometers, 1 to 100 micrometers, 1 to 50 micrometers, 1 to 25 micrometers, 1 to 10 micrometers, or 1 to 5 micrometers. The particles are often in the form of beads.

The polymeric particles usually have multiple pores distributed over the surface of the particles. In some embodiments, the polymeric particles are hollow in addition to having multiple pores distributed over the surface of the particles. After removal of the poly(propylene glycol) porogen, the resulting polymeric particles tend to be more porous than polymeric particles prepared using a first phase that is predominately water.

The porous article includes the porous polymeric particles bound to a fibrous substrate. The fibrous substrate can be either woven or nonwoven. In many embodiments, the porous article includes porous polymeric particles bound to a nonwoven, fibrous substrate. The nonwoven, fibrous substrate is often in the form of a layer of interlaid fibers that are not woven or knitted together. The nonwoven, fibrous substrate can be prepared by any suitable process such as, for example, air laying techniques, spunlaid techniques such as meltblown or spunbonding, carding, and combinations thereof. In some applications, it may be preferable to prepare the fibrous substrate by meltblown techniques.

Fibers suitable for use in preparing the nonwoven, fibrous porous matrix are usually pulpable or extrudable fibers such as those that are stable to radiation and/or to a variety of solvents. Useful fibers typically include polymeric fibers. In many embodiments, the fibers include polymeric fibers, such as one or a plurality of different types of polymeric fibers. For example, at least some of the polymeric fibers can be selected to exhibit a degree of hydrophilicity. In certain embodiments, the fibers include meltblown fibers.

Suitable polymeric fibers include those made from natural polymers (those derived from animal or vegetable sources) and/or synthetic polymers, including thermoplastic and solvent-dispersible polymers. Useful polymers include polyesters (for example, polyethylene terephthalate, polybutylene terephthalate, and polyester elastomers (e.g., those available under the trade designation HYTREL from E. I. DuPont de Nemours & Co.)); polyamides (for example, nylon 6, nylon 6,6, nylon 6,12, poly(iminoadipoyliminohexamethylene), poly(iminoadipoyliminodecamethylene), polycaprolactam, and the like); polyurethanes (for example, ester-based polyurethanes and ether-based polyurethanes); polyolefins (for example, polyethylene, polypropylene, polybutylene, copolymers of ethylene and propylene, alpha olefin copolymers such as copolymers of ethylene or propylene with 1-butene, 1-hexene, 1-octene, and 1-decene such as poly(ethylene-co-1-butene), poly(ethylene-co-1-butene-co-1-hexene), and the like); rubber elastomers such as a natural rubber (for example, polyisoprene) or a synthetic elastomer such as neoprene, butyl rubber, nitrile rubber, or silicone rubber; fluorinated polymers (for example, poly(vinyl fluoride), poly(vinylidene fluoride), copolymers of vinylidene fluoride such as poly(vinylidene fluoride-co-hexafluoropropylene), copolymers of chlorotrifluoroethylene such as poly(ethylene-co-chlorotrifluoroethylene), and the like); chlorinated polymers; poly(butadienes); polyimides (for example, poly(pyromellitimide) and the like); polyethers; poly(ether sulfones) (for example, poly(diphenylether sulfone), poly(diphenylsulfone-co-diphenylene oxide sulfone), and the like); poly(sulfones); poly(vinyl esters) such as poly(vinyl acetates); copolymers of vinyl acetate (for example, poly(ethylene-co-vinyl acetate), copolymers in which at least some of the acetate groups have been hydrolyzed to provide various poly(vinyl alcohols) including poly(ethylene-co-vinyl alcohol), and the like); poly(phosphazenes); poly(vinyl ethers); poly(vinyl alcohols); poly(carbonates); and the like; and combinations thereof.

In certain embodiments, one type of polymeric fiber is used, such as a polyester elastomer. In some embodiments, mixtures of hydrophobic and hydrophilic polymeric fibers are used. For example, the fibrous porous matrix can include a mixture of hydrophilic fibers such as polyamides plus hydrophobic fibers such as polyolefins. Further, suitable fibers for the fibrous porous matrix can include coextruded fibers such as layered fibers, fibers having a core-sheath structure, a side by side structure, an islands-in-the-sea structure or a segmented-pie structure or other types known to those skilled in the art.

The fibers used to form a fibrous substrate can be of a length and a diameter that can provide a porous substrate having structural integrity and porosity, which can be particularly useful as the fluid management article of the present disclosure. The fiber lengths are often at least about 10 millimeters, at least 15 millimeters, at least 20 millimeters, at least 25 millimeters, at least 30 millimeters, at least 50 millimeters, or at least 75 millimeters. The diameter of the fibers can be, for example, at least 1 micrometer, at least 2 micrometers, at least 5 micrometers, at least 10 micrometers, at least 20 micrometers, at least 40 micrometers, and up to 12 micrometers, up to 25 micrometers, up to 35 micrometers, or up to 50 micrometers. The fiber lengths and diameters will vary depending upon factors such as the nature of the fiber and the type of application.

The fibrous substrate can contain a plurality of different types of fibers. In some embodiments, the substrate can be formed using two, three, four, or even more different types of fibers. For example, a nylon fiber can be added for strength and integrity and hydrophilic character, while polyethylene fibers provide hydrophobic character to the substrate.

The fibrous substrate often further contains at least one polymeric binder or adhesive. Suitable polymeric binders and adhesives include natural and synthetic polymeric materials that are relatively inert (exhibiting little or no chemical interaction with either the fibers or the porous polymeric particles). Useful polymeric binders and adhesives include polymeric resins (for example, in the form of powders and latexes). Suitable polymeric resins for use in the fibrous substrate include, but are not limited to, natural rubbers, neoprene, styrene-butadiene copolymers, acrylate resins, polyvinyl chloride, polyvinyl acetate, and combinations thereof. In many embodiments, the polymeric resin includes acrylate resins.

In certain embodiments, the fibrous substrate contains only fibers. In certain alternate embodiments, the fibrous substrate contains only fibers and binder or adhesive. For example, at least 90 weight percent, at least 95 weight percent, at least 98 weight percent, at least 99 weight percent, or at least 99.5 weight percent of a dry fibrous substrate is either fibers or binder/adhesive.

The article includes both the fibrous substrate and porous polymeric particles bound to the fibrous substrate. In most embodiments, the article contains at least 5 weight percent porous polymeric particles based on a total dry weight of the article. This can be also be referred to as having a particle loading of at least 5 weight percent. If the amount of the porous polymeric particles is lower than about 5 weight percent, the article may not contain enough porous polymeric particles to effectively manage fluids. In some examples, the porous article contains at least 10 weight percent, at least 15 weight percent, at least 20 weight percent, at least 30 weight percent, at least 40 weight percent, at least 50 weight percent, at least 60 weight percent, at least 70 weight percent, or at least 80 weight percent porous polymeric particles based on a total dry weight of the porous article. In some embodiments, a particle loading of at least about 30 weight percent can be particularly suitable for optimizing wicking and evaporative properties of the resulting fluid management article.

On the other hand, the article usually contains no greater than 90 weight percent porous polymeric particles based on the total dry weight of the article. If the amount of the porous polymeric particles is greater than about 90 weight percent, the porous article may contain an insufficient amount of the fibrous substrate. That is, the strength of the porous article may be insufficient to hold together when contacted with a fluid. In some examples, the article contains no greater than 85 weight percent, no greater than 75 weight percent, no greater than 65 weight percent, no greater than 55 weight percent, no greater than 45 weight percent, no greater than 35 weight percent, or no greater than 25 weight percent porous polymeric particles based on a total weight of the porous article.

Stated differently, the article often contains 5 to 90 weight percent porous polymeric particles and 10 to 95 weight percent fibrous substrate, 15 to 90 weight percent porous polymeric particles and 10 to 85 weight percent fibrous substrate, 20 to 70 weight percent porous polymeric particles and 30 to 80 weight percent fibrous substrate, 20 to 60 weight percent porous polymeric particles and 40 to 80 weight percent fibrous substrate, 25 to 50 weight percent porous polymeric particles and 40 to 75 weight percent fibrous substrate, or 30 to 60 weight percent porous polymeric particles and 40 to 70 weight percent fibrous substrate. In one embodiment, the article contains 15 to 57 weight percent porous polymeric particles and 43 to 85 weight percent fibrous substrate. The amounts are based on the total dry weight of the article.

In many embodiments, the article (when dry) contains only porous polymeric particles and fibrous substrate. For example, the article contains at least 90 weight percent, at least 95 weight percent, at least 98 weight percent, at least 99 weight percent, or at least 99.5 weight percent combined porous polymeric particles and fibrous substrate when dry. In certain embodiments, the article (when dry) contains only porous polymeric particles, fibrous substrate, and binder and/or adhesive. For example, the article contains at least 90 weight percent, at least 95 weight percent, at least 98 weight percent, at least 99 weight percent, or at least 99.5 weight percent combined porous polymeric particles, fibrous substrate, and bind and/or adhesive, when dry. Preferably, any polymeric binder included in the fibrous substrate adheres the porous polymeric particles to the fibrous substrate in the article. In select embodiments, the article further includes an active agent adsorbed to or within at least some of the porous polymeric particles.

The porous polymeric particles or the hollow and porous polymeric particles are well suited for storage and delivery of an active agent. That is, in certain embodiments, the porous polymeric particles further include an active agent. In particular, if all of the monomers in the monomer composition are hydrophobic, the polymeric particles tend to be hydrophobic (i.e., hydrophobic polymeric particles) and can accept (e.g., be loaded with) hydrophobic active agents. If some of the monomers in the monomer composition are hydrophilic, however, the polymeric particles tend to have sufficient hydrophilic character (i.e., hydrophilic polymeric particles) to accept hydrophilic active agents. Further, if the monomer composition includes a mixture of both hydrophobic monomers and hydrophilic monomers, the porous polymeric particles tend to have sufficient hydrophobic and hydrophilic character to accept both hydrophobic and hydrophilic active agents. In some embodiments, polymeric particles having both hydrophobic and hydrophilic character can be desirable.

Some active agents of particular interest are biologically active agents. As used herein, the term "biologically active agent" refers to a compound that has some known effect on living systems such as, for example, a bacteria or other microorganism, plant, fish, insect, or mammal. The bioactive agent is added for the purpose of affecting the living system such as affecting the metabolism of the living system. Examples of biologically active agents include, but are not limited to, medicaments, herbicides, insecticides, antimicrobial agents, disinfectants and antiseptic agents, local anesthetics, astringents, antifungal agents (i.e., fungicides), antibacterial agents, growth factors, herbal extracts, antioxidants, steroids or other anti-inflammatory agents, compounds that promote wound healing, vasodilators, exfoliants, enzymes, proteins, carbohydrates, silver salts, and the like. Any other suitable biologically active agent known in the art can be used. In some particular embodiments, the active agent is an antimicrobial agent.

Any suitable method can be used to load (i.e., to position) the active agent into the porous polymeric particle once the porogen has been removed. In some embodiments, the active agent is a liquid and the polymeric particles are mixed with the liquid to load the active agent. In other embodiments, the active agent can be dissolved in a suitable organic solvent or water and the polymeric particles are exposed to the resulting solution. Any organic solvent that is used is typically selected so that it does not dissolve the polymeric particles. When an organic solvent or water is used, at least some of the organic solvent or water may be loaded by the polymeric particle in addition to the active agent.

When the active agent is dissolved in an organic solvent or water, the concentration is typically selected to be as great as possible to shorten the time needed for loading of a suitable amount of the active agent onto the porous polymeric particle. The amount of active agent loaded and the amount of time required for loading are often dependent, for example, on the composition of the monomers used to form the polymeric particle, the rigidity of the polymeric particle (e.g., the amount of crosslinking), and the compatibility of the active agent with the polymeric particle. The loading time is often less than 24 hours, less than 18 hours, less than 12 hours, less than 8 hours, less than 4 hours, less than 2 hours, less than 1 hour, less than 30 minutes, less than 15 minutes, or less than 5 minutes. After loading, the particles are typically separated from the solution containing the active agent by decantation, filtration, centrifugation, or drying.

The volume of active agent loaded can be up to the volume of poly(propylene glycol) removed from the polymerized product used to form the porous polymeric particles. That is, the active agent can fill the voids left after removal of the poly(propylene glycol). In many embodiments, the amount of active agent loaded can be up to 50 weight percent based on a total weight of the polymeric particle after loading (i.e., porous polymeric particles plus the loaded active agent). In some example loaded polymeric particles, the amount of the active agent can be up to 40 weight percent, up to 30 weight percent, up to 25 weight percent, up to 20 weight percent, up to 15 weight percent, up to 10 weight percent, or up to 5 weight percent. The amount of active agent is typically at least 0.1 weight percent, at least 0.2 weight percent, at least 0.5 weight percent, at least 1 weight percent, at least 5 weight percent, or at least 10 weight percent. Some loaded porous polymeric particles contain 0.1 to 50 weight percent, 0.5 to 50 weight percent, 1 to 50 weight percent, 5 to 50 weight percent, 1 to 40 weight percent, 5 to 40 weight percent, 10 to 40 weight percent, or 20 to 40 weight percent active agent. Because the porous polymeric particles tend to be highly crosslinked, they tend to swell little even after loading of the active agent. That is, the average sizes of the porous polymeric particles are comparable before and after loading of the active agent.

The active agent is not covalently bonded to the polymeric particles. Under suitable diffusion controlled conditions, the active agent can be released (i.e., delivered) from the polymeric particles. The release can be complete or nearly complete (e.g., greater than 90 percent, greater than 95 percent, greater than 98 percent, greater than 99 percent complete).

In most embodiments, the polymeric particles that are prepared using a second monomer or third monomer that is hydrophilic can be used as a moisture management material. That is, these hydrophilic porous polymeric particles can be used to control moisture (e.g., to adsorb moisture). As used herein, the term "moisture" refers to water or to a water-containing solution. Applications include, but are not limited to, adsorption of wound fluids in wound dressing articles, adsorption of sweat in sweat management articles, and adsorption of urine in incontinence management articles. The hydrophilic polymeric particles can be used to both manage moisture and to deliver a hydrophilic active agent. For example, hydrophilic polymeric particles can be used in a wound dressing to both manage water and to deliver a hydrophilic antimicrobial agent.

The polymeric particles are not tacky. This makes them well suited for applications where the particles are included in a layer of an article that is positioned adjacent to skin. Additionally, because the polymeric particles tend to be highly crosslinked, they tend to swell little even when an active agent is loaded or moisture is adsorbed. That is, the polymeric particles undergo a relatively small change in volume when an active agent is loaded or moisture is adsorbed.

Advantageously, the article comprising a fibrous substrate and porous polymeric particles bound to the fibrous substrate tends not to swell when fluid is absorbed. For instance, upon immersion in water for 1 hour, the article does not expand in length in any direction. The article further provides enhanced wicking and evaporation abilities as compared to the fibrous substrate without porous polymeric particles bound to the fibrous substrate. This is discussed in the Examples below. Without wishing to be bound by theory, it is believed that the spherical shape and tortuosity of surface of the porous polymeric particles result in a structure that not only breaks the surface tension of many fluids but also results in an increased capillary action that facilitates the transport of fluids throughout the article. The combined effect of the action of the morphology of the particles and their placement in the fibrous substrate results in much higher wicking and evaporation rates than other fibrous substrates.

A method of making fluid management articles of the present disclosure will now be described. The method includes a) providing porous polymeric particles; b) providing a fibrous substrate comprising fibers; and c) binding the porous polymeric particles to the fibrous substrate. At least 50% of the porous polymeric particles are bound to the fibrous substrate. The porous polymeric particles comprise a polymerized product of a reaction mixture comprising i) a monomer composition comprising at least 10 weight percent of a first monomer of Formula (I) based on a total weight of the monomer composition; and ii) a poly(propylene glycol) having a weight average molecular weight of at least 500 grams/mole.

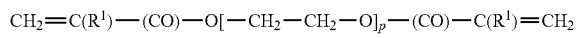

(I)

In Formula (I), p is an integer equal to at least 1 and $R^1$ is hydrogen or alkyl. The poly(propylene glycol) is removed from the polymerized product to provide the porous polymeric particles.

In certain embodiments, binding porous polymeric particles to the fibrous substrate comprises i) heating the fibrous substrate to a temperature above the glass transition temperature of the fibers; ii) contacting the porous polymeric particles with the heated fibrous substrate; and iii) cooling the porous polymeric particles and fibrous substrate to fuse porous polymeric particles to the fibrous substrate. In such embodiments, the fibrous substrate is made by any suitable method known to the skilled practitioner (for example, air laying techniques, spunlaid techniques such as meltblown or spunbonding, carding, and the like). An advantage of this method is that porous polymeric particles can be bound to any available fibrous substrate, and without requiring binders and/or adhesives. In one embodiment, the fibrous substrate comprises fibers having a lower glass transition temperature than the degradation temperature of the porous polymeric particles. Selecting such fibers will minimize the likelihood of damaging the porous polymer particles when they are brought into contact with the heated fibers.

Figure 5:
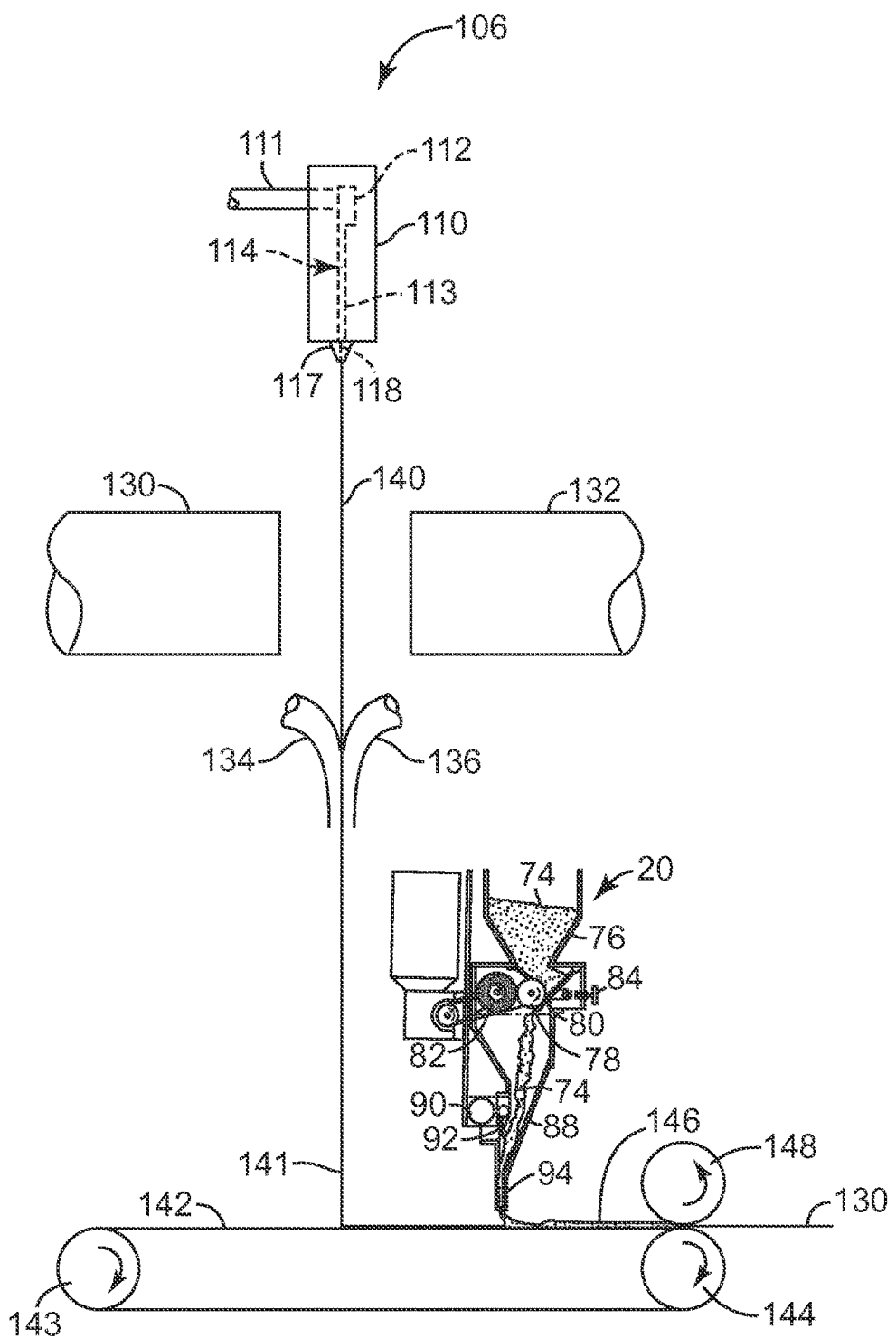
FIG. 5 is a schematic of an experimental setup for preparing fluid management articles.

Referring to FIG. 5, one suitable apparatus 106 is illustrated for making a fluid management article using a spun bond process. Molten fiber-forming polymeric material enters generally vertical nonwoven die 110 via inlet 111, flows downward through manifold 112 and die slot 113 of die cavity 114 (all shown in phantom), and exits die cavity 114 through orifices such as orifice 118 in die tip 117 as a series of downwardly-extending filaments 140. A quenching fluid (typically air) conducted via ducts 130 and 132 solidifies at least the surfaces of the filaments 140. The at least partially solidified filaments 140 are drawn toward collector 142 while being attenuated into fibers 141 by generally opposing streams of attenuating fluid (typically air) supplied under pressure via ducts 134 and 136. Meanwhile, referring to the apparatus 20, porous particles 74 pass through hopper 76 past feed roll 78 and doctor blade 80, which is adjusted with doctor blade adjustment 84. A stream of particles 74 is directed through nozzle 94 amidst fibers 141. The mixture of particles 74 and fibers 141 lands against porous collector 142 carried on rollers 143 and 144 and forms a spun bond web 146. Calendaring roll 148 opposite roll 144 compresses and point-bonds the fibers in web 146 to produce the fluid management article 130, which is a calendared spun bond nonwoven particle-loaded web. Further details regarding the manner in which spun bonding would be carried out using such an apparatus will be familiar to those skilled in the art.

In certain embodiments, binding porous polymeric particles to a fibrous substrate is performed simultaneously with the providing of a fibrous substrate. In one specific method, the article is prepared using a meltblown process. The meltblown process includes flowing molten polymer through a plurality of orifices to form filaments; attenuating the filaments into fibers; directing a stream of porous polymeric particles amidst the filaments or fibers; and collecting the fibers and porous polymeric particles as a nonwoven web to form an article. The meltblown fibers and the porous polymeric particles are optionally collected on a vacuum collection drum roll. In one embodiment, the method further comprises compressing the nonwoven web by calendaring, heating, or applying pressure to form a compressed web.

The particle loading process is an additional processing step to a standard meltblown fiber forming process, as disclosed in, for example, commonly assigned U.S. Patent Publication No. 2006/0096911. Blown microfibers (BMF) are created by a molten polymer entering and flowing through a die, the flow being distributed across the width of the die in the die cavity and the polymer exiting the die through a series of orifices as filaments. In one embodiment, a heated air stream passes through air manifolds and an air knife assembly adjacent to the series of polymer orifices that form the die exit (tip). This heated air stream can be adjusted for both temperature and velocity to attenuate (draw) the polymer filaments down to the desired fiber diameter. The BMF fibers are conveyed in this turbulent air stream towards a rotating surface where they collect to form a web.

The porous polymeric particles are loaded into a particle hopper (or dropper) where they gravimetrically fill recessed cavities in a feed roll. A rigid or semi-rigid doctor blade with segmented adjustment zones forms a controlled gap against the feed roll to restrict the flow out of the hopper. The doctor blade is normally adjusted to contact the surface of the feed roll to limit particle flow to the volume that resides in the recesses of the feed roll. The feed rate can then be controlled by adjusting the speed that the feed roll turns. A brush roll operates behind the feed roll to remove any residual particles from the recessed cavities. The particles fall into a chamber that can be pressurized with compressed air or other source of pressured gas. This chamber is designed to create an airstream that will convey the particles and cause the porous polymeric particles to mix with the meltblown fibers being attenuated and conveyed by the air stream exiting the meltblown die.

In certain embodiments, binding of the porous polymeric particles to the fibrous substrate and the providing a fibrous substrate comprises i) extruding meltblown fibers comprising a polymeric material; ii) metering porous polymeric particles into the meltblown fibers; and iii) collecting the meltblown fibers and the porous polymeric particles as a nonwoven fibrous substrate comprising porous polymeric particles bound to the fibrous substrate.

By adjusting the pressure in the forced air particle stream, the velocity distribution of the particles is changed. When very low particle velocity is used, the particles may be diverted by the die airstream and not mix with the fibers. At low particle velocities, the particles may be captured only on the top surface of the web. As the particle velocity increases, the particles begin to more thoroughly mix with the fibers in the meltblown airstream and can form a uniform distribution in the collected web. As the particle velocity continues to increase, the particles partially pass through the meltblown airstream and are captured in the lower portion of the collected web. At even higher particle velocities, the particles can totally pass through the meltblown airstream without being captured in the collected web.

In another embodiment, the porous polymeric particles are sandwiched between two filament airstreams by using two generally vertical, obliquely-disposed dies that project generally opposing streams of filaments toward the collector. Meanwhile, particles pass through the hopper and into a first chute. The particles are gravity fed into the stream of filaments. The mixture of particles and fibers lands against the collector and forms a nonwoven web.

In other embodiments, the particles are provided using a vibratory feeder, eductor, or other techniques known to those skilled in the art.

The resulting article is a dry sheet having an average thickness of at least 50 micrometers, at least 100 micrometers, at least 250 micrometers, at least 500 micrometers, at least 800 micrometers, at least 1,500 micrometers, or at least 2,500 micrometers. The average thickness is often up to 3,000 micrometers, up to 2,000 micrometers, up to 1,000 micrometers, up to 600 micrometers, up to 400 micrometers, or up to 300 micrometers.

In the article, at least some of the porous polymeric particles are bound in the fibrous substrate through either fusing (direct connection between the particles and the substrate) or adhering via adhesives and/or binders, depending upon the nature of the fibers that are utilized. In certain embodiments, at least 50% of the porous polymeric particles are bound to the fibrous substrate. Stated another way, up to 50% of the porous polymeric particles can be entrapped in the fibrous substrate without being fused to one or more fibers or adhered to the fibrous substrate with an adhesive or a binder. In some embodiments, at least 25% of the porous polymeric particles, or at least 30%, or at least 40%, or at least 50%, or at least 60%, or at least 70% of the porous polymeric particles are fused to the fibrous substrate. The porous polymeric particles are often preferably distributed essentially uniformly throughout the fibrous substrate within the article.

Generally the average pore size of the dry porous article can be in a range of 0.1 to 10 micrometers, as measured by scanning electron microscopy (SEM). Void volumes in the range of 20 to 80 volume percent or in a range of 40 to 60 volume percent can be useful. The porosity of the article can be modified (increased) by using fibers of larger diameter or stiffness in the fibrous substrate.

The porous article can be flexible (for example, it can be a porous sheet rolled around a 0.75 inch (about 2 cm) diameter core). This flexibility can enable the sheet to be pleated, folded, or rolled. The porous sheet has an open pore structure that tends to provide minimal resistance to the passage of fluid. Because of this minimal resistance, relatively high volumes of liquid can be relatively quickly passed through it.

Methods of Using Medical Dressings

Medical dressings of the present disclosure, such as those illustrated in FIGS. 1-3, can be applied to (i.e., over) a target site to protect the target site. The medical dressing can be applied to the target site, such that the fluid management article is in fluid communication with the target site.

For example, in some embodiments, the fluid management article (e.g., the fluid management article 130 of FIG. 1) can be positioned in direct contact with the target site. In some embodiments, the fluid management article (e.g., the fluid management article 230 of FIG. 2) can be positioned in indirect contact but fluid communication with the target site, e.g., via an absorbent core (e.g., the absorbent core 235).

Furthermore, in some embodiments, the fluid management article can be positioned in indirect contact but fluid communication with the target site, e.g., when at least a portion of the medical dressing is in contact with the target site, and the fluid management article is in fluid communication with the portion of the medical dressing that is in contact with the target site. For example, with reference to FIG. 3, in some embodiments, the medical dressing 300 can be positioned over the target site (e.g., an insertion site) such that the backing 310 is in direct contact (or indirect contact via an absorbent core) with the target site, and the fluid management article 330 forms a portion of the same medical dressing 300 and is located in the medical dressing 300 in such a way that fluid can flow from the target site to the fluid management article 330. For example, as shown in FIG. 3, the backing adhesive 316 can be patterned to provide channels or pathways from the target site to the fluid management article 330 (e.g., to the inner periphery or edges of the opening 345 in the fluid management article 330).

The above examples and the embodiments in FIGS. 1-3 are described and illustrated herein by way of example only, and it should be understood that other configurations are possible and within the scope of the present disclosure.

Methods of applying medical dressings of the present disclosure can further include removing any liners, tabs, frames, or carrier layers that may be present. For example, a release liner can be removed to expose one or both of the skin-contact adhesive on the fluid management article and the backing adhesive; the medical dressing can be applied to a target site while the tabs, frames or carrier layers remain coupled to the dressing for added support or reinforcement; and finally, any tabs, frames, or carrier layers can be removed (e.g., from the backing). Any additional tapes or strips can also then be adhered to or around the medical dressing, as needed for a particular application.

Tabs, Frames or Carrier Layers

The material used to form any tabs, frames or carrier layers employed in medical dressings of the present disclosure is generally substantially more rigid than the backings to prevent the backings from improperly wrinkling during application to a patient. The tabs, frames or carrier layers, if employed, can be heat-sealable to the first major surface of the backing with or without a low adhesion backsize coating described above. In general, the tab, frame or carrier layer materials can include, but are not limited to, polyethylene/vinyl acetate copolymer-coated papers and polyester films. One example of a suitable material is a polyethylene/vinyl acetate copolymer coated super calendared Kraft paper (1-80BKG-157 PE; LOPAREX of Willowbrook, Ill.).

In some embodiments, the tabs, frames or carrier layers can include perforations to aid in separating portions thereof after application of the medical dressing to a patient. Spacing and shape of the perforations are adjusted to provide a layer with relatively easy to tear performance on removal of the layer from the applied dressing. The perforations may be shaped in accordance with any of the accepted perforation patterns including linear, angled, Y-shaped, V-shaped, dual-angled offset, sinusoidal, etc.

Release Liners

Release liners suitable for use with the medical dressings of the present disclosure can include, but are not limited to, kraft papers, polyethylene, polypropylene, polyester, or combinations thereof. Such liners can be coated with release agents, such as fluorochemicals, silicones, or other suitable low surface energy materials. Other adhesives and release liner combinations known to those of ordinary skill in the art can also be employed in the medical dressings of the present disclosure. Examples of commercially available silicone coated release papers are POLYSLIK™, silicone release papers available from Rexam Release (Bedford Park, Ill.) and silicone release papers supplied by LOPAREX (Willowbrook, Ill.). Other non-limiting examples of such release liners commercially available include siliconized polyethylene terephthalate films, commercially available from H. P. Smith Co., and fluoropolymer coated polyester films, commercially available from 3M Company (St. Paul) under the brand "SCOTCHPAK™" release liners.

Adhesives

As described above, in some embodiments, the backing adhesive can have an adhesion that is greater than the skin-contact adhesive, i.e., the adhesive on the second major surface of the fluid management article. In some embodiments, the backing adhesive and the skin-contact adhesive may be of the same or similar classes of adhesive, but have different adhesion levels. For example, the backing adhesive and/or the skin-contact adhesive may be an acrylate, silicone, urethane, hydrogel, hydrocolloid, natural rubber, or synthetic rubber. Adhesion can also be tuned through changes in adhesive composition, adhesive thickness, or adhesive surface area (e.g., by employing a pattern-coated adhesive).

As mentioned above, in some embodiments the skin-contact adhesive, or the adhesive provided on the fluid management article can be provided by the fibrous substrate of the fluid management article itself. However, in some embodiments, the fluid management article can additionally or alternatively include a separate adhesive that is applied (e.g., coated) onto the fluid management article (e.g., onto its second major surface that is configured to be applied to skin).

"Adhesion" refers to the force required to separate an adhesive from an underlying substrate. Adhesion can be measured in a number of ways. For example, adhesion can be defined by peel force or shear force. In some embodiments, adhesion can be defined by peel adhesion using ASTM D3330/D3330M-04(2010). In some embodiments, adhesion can be defined by shear adhesion using ASTM D3654M-06(2011). Adhesion is highly dependent on the specific substrate being adhered to, as well as the time the pressure-sensitive adhesive (PSA) is allowed to dwell on the substrate.

For example, typical peel adhesion values exhibited by pressure-sensitive adhesives in medical dressings maybe in the range of 20 to 300 g/cm as measured from stainless steel. In some embodiments, at least 10% higher peel adhesion, as measured by ASTM D3330/D3330M-04(2010), of the backing adhesive over the skin-contact adhesive may realize the benefit of both securing to the fluid management article, while providing gentle adhesion to the skin.

In some embodiments, the backing adhesive can be an acrylate adhesive and the skin-contact adhesive can be a silicone adhesive or an acidic adhesive (e.g., acrylic acid-based). For example, in some embodiments, the backing adhesive can be an isooctyl acrylate:acrylamide ("IOA-acrylamide") adhesive, and the skin-contact adhesive can be an isooctyl acrylate:acrylic acid ("IOA:AA") adhesive. In some embodiments, the backing adhesive and the skin-contact adhesive can both include an IOA:AA adhesive. In some embodiments, any of the above adhesive combinations can be employed, but with 2-ethyl hexyl acrylate ("2-EHA") substituted for IOA.

The term "acrylate" or "acrylate-based" or "acrylate-containing" refers to monomeric acrylic or methacrylic esters of alcohols. Acrylate and methacrylate monomers are referred to collectively herein as "acrylate" monomers. Materials that are described as "acrylate-based" or "acrylate-containing" contain, or are derived from, at least some acrylate monomers and may contain additional co-monomers.

The term "acrylic acid" or "acrylic acid-based" or "acrylic acid-containing" refers to monomers comprising acrylic acid. Acrylic acid monomers are referred to collectively herein as "acrylic acid" monomers. Materials that are described as "acrylic acid-based" or "acrylic acid-containing" contain, or are derived from, at least some acrylic acid monomers and may contain additional co-monomers. This class of adhesives also falls within the broader class of acidic adhesives (i.e., adhesives comprising an acidic component), and in some embodiments, the skin-contact adhesive of the fluid management article can include an acidic adhesive, and particularly, an acrylic acid-based adhesive.

Suitable acrylate adhesives that can be applied to skin such as the acrylate copolymers are described in U.S. Pat. No. RE 24,906, the disclosure of which is hereby incorporated by reference. In particular, a 97:3 iso-octyl acrylate:acrylamide copolymer. Another acrylate adhesive is an 70:15:15 isooctyl acrylate:ethyleneoxide acrylate:acrylic acid terpolymer, as described in U.S. Pat. No. 4,737,410 (Example 31), the disclosure of which is hereby incorporated by reference. Other useful acrylate adhesives are described in U.S. Pat. Nos. 3,389,827, 4,112,213, 4,310,509, and 4,323,557, the disclosures of which are incorporated herein by reference.

The term "silicone" or "silicone-based" or "silicone-containing" refers to polymers that contain units with dialkyl or diaryl siloxane ($—SiR_2O—$) repeating units. The silicone-based polymers may be segmented copolymers or polysiloxanes polymers. The terms silicone and siloxane are used interchangeably.

Generally, silicone adhesives are able to effectively secure materials or substrates to skin and upon removal from the skin produce little or no skin damage. In some embodiments, one or both of the backing adhesive and the skin-contact adhesive on the fluid management article can include a silicone adhesive.

Examples of suitable silicone adhesive systems can include, but are not limited to, products available under the following trade designations: Dow Corning MG 7-9850, Wacker SILPURAN® 2110 and 2130, Bluestar SILBIONE® RT Gel 4317 and 4320, Nusil MED-6345 and 6350. Other examples of suitable silicone adhesives are disclosed in PCT Publications WO2010/056541, WO2010/056543 and WO2010/056544, the disclosures of which are incorporated herein by reference.

For skin-contact adhesives (and backing adhesives when used in contact with the skin), it is desirable that the adhesive is able to transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as perforating the adhesive or pattern coating the adhesive, as described in U.S. Pat. No. 4,595,001 and U.S. Pat. App. Pub. 2008-0233348, the disclosures of which are incorporated herein by reference. As mentioned above, in some embodiments, each of the backing and skin-contact adhesives can optionally be applied in a patterned or discontinuous manner.

Absorbent Cores

Absorbent cores of the present disclosure can include a foam or gel. Examples of suitable foams are described, e.g., in U.S. Pat. Nos. 6,881,875 and 6,977,323, each of which is incorporated by reference herein. Examples of suitable gels (e.g., hydrogels) are described in U.S. Publication No. 2009/0187130, and U.S. Pat. No. 7,005,143, each of which is incorporated herein by reference.

The absorbent core can include any material that is conformable, non-irritating to the wearer's skin, and capable of absorbing and retaining liquids. The absorbent core may be a single layer or multilayer material, wherein if it is a multilayer material each layer may be of the same material or of different materials.

Examples of materials that would be suitable for the absorbent core include creped cellulose wadding; meltblown polymers; chemically stiffened, modified or cross-linked cellulosic fibers; tissue; absorbent foams; absorbent sponges; superabsorbent polymers; absorbent gelling materials; or any other known absorbent material or combinations of materials. The absorbent core may further comprise minor amounts (typically less than 10%) of non-liquid absorbent materials, such as adhesives, waxes, oils, antimicrobials, active ointments, and the like, for example.

In some embodiments, the absorbent core can be an open-cell foam. The foam may include a synthetic polymer that is adapted to form a conformable open-cell foam that absorbs the wound exudate. Examples of suitable materials for the foams include synthetic organic polymers including, but not limited to: polyurethanes, carboxylated butadiene-styrene rubbers, polyesters, and polyacrylates. The polymeric foams can be made of one or more types of monomers (e.g., copolymers) or mixtures (e.g., blends) of polymers. Examples of foam materials are described in the book entitled *Flexible Polyurethane Foams*, Dow Polyurethanes, editors R. Herrington and K. Hock, 1997.

The foams can be of a wide range of thicknesses; from about 0.5 mm or 1 mm to about 30 mm or 80 mm thick. Furthermore, they can include one or more layers tailored to have the desired properties. These layers can be directly bonded to each other or bonded together with adhesive layers. Optionally, disposed between these layers can be one or more layers of polymeric netting or nonwoven, woven, or knit webs for enhancing the physical integrity of the foam. In some embodiments, the second surface of the absorbent core can include a foam with a skin to prevent fluid passage through the absorbent core.

In some embodiments, the absorbent core can include superabsorbing particles or fibers contained within a porous pouch. Examples include superabsorbent fibrous webs that are available from National Nonwovens, Cincinnati, Ohio, or sachets containing superabsorbent material such as Sorbion Sachet S available from Sorbion AG, Senden, Germany.

In some embodiments, the absorbent body can include a wound-contacting layer bonded to the skin-facing surface of the absorbent core. Examples of such wound-contacting layers include polymeric netting and porous (e.g., perforated) films, or other conventional materials that prevent the dressing from sticking to the wound. Such a wound-contacting layer can be bonded directly to the absorbent core (e.g., cast or thermomechanical bonding), or bonded to the absorbent core using an adhesive layer, for example.

One example of a suitable absorbent core is found in a 3M Tegaderm™ High Performance Foam Dressing available from 3M Company of St. Paul, Minn. Suitable constructions for the absorbent core are disclosed in U.S. Pat. Nos. 6,838,589; 7,030,288; and 7,612,248, the disclosures of which are herein incorporated by reference.

The following embodiments are intended to be illustrative of the present disclosure and not limiting.

First Set of Exemplary Embodiments of the Medical Dressings of the Present Disclosure Embodiment 1 is a medical dressing comprising:
a fluid management article comprising:
1) a fibrous substrate; and
2) porous polymeric particles, wherein at least 50% of the porous polymeric particles are bound to the fibrous substrate, wherein the porous polymeric particles comprise a polymerized product of a reaction mixture comprising:
   a) a first phase having a first volume and comprising
      i) a compound of Formula (II)

$$HO(-CH_2CH(OH)CH_2O)_n-H \quad (II)$$

wherein n is an integer equal to at least 1, and
      ii) a nonionic surfactant; and
   b) a second phase having a second volume and being dispersed in the first phase, wherein the first volume is greater than the second volume and wherein the second phase comprises
      i) a monomer composition comprising at least 10 weight percent of a first monomer of Formula (I)

$$CH_2=C(R^1)-(CO)-O[-CH_2-CH_2-O]_p-(CO)-C(R^1)=CH_2 \quad (I)$$

based on a total weight of the monomer composition, wherein p is an integer equal to at least 1 and $R^1$ is hydrogen or alkyl, and
      ii) a poly(propylene glycol) having a weight average molecular weight of at least 500 grams/mole, wherein the poly(propylene glycol) does not form a portion of the polymerized product.

Embodiment 2 is the medical dressing of embodiment 1, further comprising a backing configured to cover at least a portion of the fluid management article.

Embodiment 3 is the medical dressing of embodiment 2, wherein the backing includes a compression dressing.

Embodiment 4 is the medical dressing of embodiment 2 or 3, wherein the backing includes a first major surface and a second major surface opposite the first major surface, the second major surface comprising a backing adhesive, the backing adhesive being coupled to the first major surface of the fluid management article.

Embodiment 5 is the medical dressing of embodiment 1, wherein the fluid management article includes a first major surface and a second major surface opposite the first major surface, the second major surface comprising a skin-contact adhesive.

Embodiment 6 is the medical dressing of embodiment 5, wherein the, the skin-contact adhesive is pattern coated on the second major surface of the fluid management article.

Embodiment 7 is the medical dressing of embodiment 5 or 6, wherein the skin-contact adhesive is provided by at least a portion of the fibrous substrate.

Embodiment 8 is the medical dressing of any of embodiments 5-7, further comprising a backing configured to cover at least a portion of the fluid management article.

Embodiment 9 is the medical dressing of embodiment 8, wherein the backing includes a first major surface and a second major surface opposite the first major surface, the second major surface comprising a backing adhesive, the backing adhesive being coupled to the first major surface of the fluid management article.

Embodiment 10 is the medical dressing of embodiment 9, wherein the backing adhesive comprises an acrylate-based adhesive, and the skin-contact adhesive comprises an acidic adhesive.

Embodiment 11 is the medical dressing of any of embodiments 1-10, wherein the porous polymeric particles are substantially free of the polypropylene glycol).

Embodiment 12 is the medical dressing of embodiment 4 or 9, wherein the backing adhesive is patterned.

Embodiment 13 is the medical dressing of any of embodiments 4, 9 and 12, wherein the backing adhesive comprises an acrylate-based adhesive.

Embodiment 14 is the medical dressing of any of embodiments 5-13, wherein the skin-contact adhesive comprises an acrylic acid-based adhesive.

Embodiment 15 is the medical dressing of any of embodiments 1-14, wherein the medical dressing comprises at least one of a wound dressing and an IV dressing.

Embodiment 16 is the medical dressing of any of embodiments 1-15, wherein the fluid management article comprises a particle loading of at least about 10%.

Embodiment 17 is the medical dressing of any of embodiments 1-16, wherein the fibrous substrate comprises meltblown fibers.

Embodiment 18 is the medical dressing of any of embodiments 1-17, wherein the fibrous substrate comprises fibers selected from polyolefins, polyesters, polyamides, polyurethanes, rubber elastomers, or combinations thereof.

Embodiment 19 is the medical dressing of any of embodiments 1-18, wherein the monomer composition further comprises a second monomer of Formula (III) or Formula (IV)

$$CH_2=CR^1-(CO)-O-Y-R^2 \quad (III)$$

$$CH_2=CR^1-(CO)-O-R^3 \quad (IV)$$

wherein
R$^1$ is hydrogen or methyl;
Y is a single bond, alkylene, oxyalkylene, or poly(oxyalkylene);
R$^2$ is a carbocyclic group or heterocyclic group; and
R$^3$ is a linear or branched alkyl.

Embodiment 20 is the medical dressing of any of embodiments 1-19, wherein the monomer composition further comprises a second monomer that is a hydroxyl-containing monomer of Formula (V) or Formula (VI).

$$CH_2=CR^1-(CO)-O-R^4 \quad (V)$$

$$CH_2=CR^1-(CO)-O-R^5-O-Ar \quad (VI)$$

wherein
R$^1$ is hydrogen or methyl;
R$^4$ is an alkyl substituted with one or more hydroxyl groups or is a group of formula $-(CH_2CH_2O)_qCH_2CH_2OH$ where q is an integer equal to at least 1; and
R$^5$ is an alkylene substituted with at least one hydroxyl group and the group Ar is an aryl group.

Embodiment 21 is the medical dressing of any of embodiments 1-20, wherein an active agent comprising an antimicrobial agent or moisture is adsorbed within at least some of the pores of the porous polymeric particles.

Embodiment 22 is the medical dressing of any of embodiments 1-21, wherein at least some of the porous polymeric particles are bound to the fibrous substrate with an adhesive, a binder, or a combination thereof.

Embodiment 23 is the medical dressing of any of embodiments 1-22, further comprising an absorbent core.

Embodiment 24 is the medical dressing of any of embodiments 1-23, wherein the fibrous substrate comprises fibers selected from polyethylene, polypropylene, polybutylene, polyethylene terephthalate, polybutylene terephthalate, nylon 6, nylon 66, polyester elastomers, or combinations thereof.

Embodiment 25 is the medical dressing of any embodiments 1-24, wherein the porous polymeric particles comprise an average diameter in the range of 1 micrometers (μm) to 100 μm.

Embodiment 26 is the medical dressing of any of embodiments 1-25, wherein upon immersion in water for 1 hour, the fluid management article does not expand in length in any direction.

Embodiment 27 is the medical dressing of any of embodiments 1-26, wherein the medical dressing is an island dressing.

Embodiment 28 is a method of moving fluid away from a target site, the method comprising applying the medical dressing of any of embodiments 1-27 to the target site, such that the fluid management article is in fluid communication with the target site.

Embodiment 29 is the method of embodiment 28, wherein the medical dressing is applied to the target site, such that the fluid management article is in direct contact with the target site.

Second Set of Exemplary Embodiments of the Medical Dressings of the Present Disclosure Embodiment 1 is a medical dressing comprising:
a backing comprising a first major surface and a second major surface opposite the first major surface, the second major surface comprising a backing adhesive;
a fluid management article having a first major surface and a second major surface, the backing adhesive being coupled to the first major surface of the fluid management article, the second major surface of the fluid management article comprising a skin-contact adhesive, the skin-contact adhesive being patterned on the second major surface, the fluid management article comprising:
1) a fibrous substrate; and
2) porous polymeric particles, wherein at least 50% of the porous polymeric particles are bound to the fibrous substrate, wherein the porous polymeric particles comprise a polymerized product of a reaction mixture comprising:
   a) a first phase having a first volume and comprising
      i) a compound of Formula (II)

$$\mathrm{HO(\!-\!CH_2CH(OH)CH_2O)}_n\!-\!\mathrm{H} \qquad (II)$$

wherein n is an integer equal to at least 1, and
   ii) a nonionic surfactant; and
   b) a second phase having a second volume and being dispersed in the first phase, wherein the first volume is greater than the second volume and wherein the second phase comprises
      i) a monomer composition comprising at least 10 weight percent of a first monomer of Formula (I)

$$\mathrm{CH_2}\!=\!\mathrm{C(R^1)}\!-\!(CO)\!-\!O[\!-\!CH_2\!-\!CH_2\!-\!O]_p\!-\!(CO)\!-\!C(R^1)\!=\!CH_2 \qquad (I)$$

based on a total weight of the monomer composition, wherein p is an integer equal to at least 1 and $R^1$ is hydrogen or alkyl, and
   ii) a poly(propylene glycol) having a weight average molecular weight of at least 500 grams/mole, wherein the poly(propylene glycol) does not form a portion of the polymerized product.

Embodiment 2 is the medical dressing of embodiment 1, wherein the porous polymeric particles are substantially free of the poly(propylene glycol).

Embodiment 3 is the medical dressing of embodiment 1 or 2, wherein the backing adhesive is patterned.

Embodiment 4 is the medical dressing of any of embodiments 1-3, wherein the backing adhesive comprises an acrylate-based adhesive.

Embodiment 5 is the medical dressing of any of embodiments 1-4, wherein the skin-contact adhesive comprises an acrylic acid-based adhesive.

Embodiment 6 is the medical dressing of any of embodiments 1-5, wherein the medical dressing comprises at least one of a wound dressing and an IV dressing.

Embodiment 7 is the medical dressing of any of embodiments 1-6, wherein the fluid management article comprises a particle loading of at least about 30%.

Embodiment 8 is the medical dressing of any of embodiments 1-7, wherein the fibrous substrate comprises meltblown fibers.

Embodiment 9 is the medical dressing of any of embodiments 1-8, wherein the fibrous substrate comprises fibers selected from polyolefins, polyesters, polyamides, polyurethanes, rubber elastomers, or combinations thereof.

Embodiment 10 is the medical dressing of any of embodiments 1-9, wherein the fibrous substrate comprises fibers selected from polyethylene, polypropylene, polybutylene, polyethylene terephthalate, polybutylene terephthalate, nylon 6, nylon 66, polyester elastomers, or combinations thereof.

Embodiment 11 is the medical dressing of any of embodiments 1-10, wherein the monomer composition further comprises a second monomer of Formula (III) or Formula (IV)

$$\mathrm{CH_2}\!=\!\mathrm{CR^1}\!-\!(CO)\!-\!O\!-\!Y\!-\!R^2 \qquad (III)$$

$$\mathrm{CH_2}\!=\!\mathrm{CR^1}\!-\!(CO)\!-\!O\!-\!R^3 \qquad (IV)$$

wherein
$R^1$ is hydrogen or methyl;
Y is a single bond, alkylene, oxyalkylene, or poly(oxyalkylene);
$R^2$ is a carbocyclic group or heterocyclic group; and
$R^3$ is a linear or branched alkyl.

Embodiment 12 is the medical dressing of any of embodiments 1-11, wherein the monomer composition further comprises a second monomer that is a hydroxyl-containing monomer of Formula (V) or Formula (VI).

$$\mathrm{CH_2}\!=\!\mathrm{CR^1}\!-\!(CO)\!-\!O\!-\!R^4 \qquad (V)$$

$$\mathrm{CH_2}\!=\!\mathrm{CR^1}\!-\!(CO)\!-\!O\!-\!R^5\!-\!O\!-\!Ar \qquad (VI)$$

wherein
$R^1$ is hydrogen or methyl;
$R^4$ is an alkyl substituted with one or more hydroxyl groups or is a group of formula $-(CH_2CH_2O)_qCH_2CH_2OH$ where q is an integer equal to at least 1; and
$R^5$ is an alkylene substituted with at least one hydroxyl group and the group Ar is an aryl group.

Embodiment 13 is the medical dressing of any of embodiments 1-12, wherein an active agent comprising an antimicrobial agent or moisture is adsorbed within at least some of the pores of the porous polymeric particles.

Embodiment 14 is the medical dressing of any of embodiments 1-13, wherein at least some of the porous polymeric particles are bound to the fibrous substrate with an adhesive, a binder, or a combination thereof.

Embodiment 15 is the medical dressing of any of embodiments 1-14, wherein the porous polymeric particles comprise an average diameter in the range of 1 micrometers (μm) to 100 μm.

Embodiment 16 is the medical dressing of any of embodiments 1-15, wherein upon immersion in water for 1 hour, the fluid management article does not expand in length in any direction.

Embodiment 17 is the medical dressing of any of embodiments 1-16, further comprising an absorbent core.

Embodiment 18 is the medical dressing of any of embodiments 1-17, wherein the medical dressing is an island dressing.

Embodiment 19 is a method of moving fluid away from a target site, the method comprising applying the medical dressing of any of embodiments 1-16 to the target site, such that the fluid management article is in fluid communication with the target site.

Embodiment 20 is the method of embodiment 19, wherein the medical dressing is applied to the target site, such that the fluid management article is in direct contact with the target site.

Exemplary Embodiments of the Fluid Management Articles of the Present Disclosure Embodiment 1 is an article that includes 1) a fibrous substrate and 2) porous polymeric particles, wherein at least 50% of the porous polymeric particles are bound to the fibrous substrate. The porous polymeric particles include a polymerized product of a reaction mixture that contains i) a monomer composition and ii) a poly(propylene glycol) having a weight average molecular weight of at least 500 grams/mole. The monomer composition contains at least 10 weight percent of a first monomer of Formula (I) based on a total weight of the monomer composition.

$$CH_2{=}C(R^1){-}(CO){-}O[{-}CH_2{-}CH_2{-}O]_p{-}(CO){-}C(R^1){=}CH_2 \qquad (I)$$

In Formula (I), the variable p is an integer equal to at least 1 and $R^1$ is hydrogen or alkyl. The poly(propylene glycol) is removed from the polymerized product to provide the porous polymeric particles.

Embodiment 2 is the article of embodiment 1, wherein the fibrous substrate is nonwoven.

Embodiment 3 is the article of embodiment 1 or 2, wherein the fibrous substrate includes meltblown fibers.

Embodiment 4 is the article of any of embodiments 1 to 3, wherein the fibrous substrate includes fibers selected from polyolefins, polyesters, polyamides, polyurethanes, rubber elastomers, or combinations thereof.

Embodiment 5 is the article of any of embodiments 1 to 4, wherein the fibrous substrate includes fibers selected from polyethylene, polypropylene, polybutylene, polyethylene terephthalate, polybutylene terephthalate, nylon 6, nylon 66, polyester elastomers, or combinations thereof.

Embodiment 6 is the article of any of embodiments 1 to 5, wherein the fibrous substrate includes fibers having a lower glass transition temperature than the degradation temperature of the porous polymeric particles.

Embodiment 7 is the article of any of embodiments 1 to 6, wherein the reaction mixture used to form the porous polymeric particles includes (a) a first phase and (b) a second phase dispersed in the first phase, wherein a volume of the first phase is greater than a volume of the second phase. The first phase contains (i) a compound of Formula (II) and (ii) a nonionic surfactant.

$$HO[{-}CH_2{-}CH(OH){-}CH_2{-}O]_n{-}H \qquad (II)$$

In Formula (II), the variable n is an integer equal to at least 1. The second phase contains (i) a monomer composition comprising the monomer of Formula (I) and (ii) a poly(propylene glycol) having a weight average molecular weight of at least 500 grams/mole.

$$CH_2{=}C(R^1){-}(CO){-}O[{-}CH_2{-}CH_2{-}O]_p{-}(CO){-}C(R^1){=}CH_2 \qquad (I)$$

In Formula (I), the variable p is an integer equal to at least 1 and $R^1$ is hydrogen or methyl. The poly(propylene glycol) is removed from the polymerized product to provide the porous polymeric particles.

Embodiment 8 is the article of any of embodiments 1 to 7, wherein the monomer composition further contains a second monomer having one (meth)acryloyl group.

Embodiment 9 is the article of any of embodiments 1 to 8, wherein the monomer composition further contains a second monomer of Formula (III) or Formula (IV)

$$CH_2{=}CR^1{-}(CO){-}O{-}Y{-}R^2 \qquad (III)$$

$$CH_2{=}CR^1{-}(CO){-}O{-}R^3 \qquad (IV)$$

In Formula (III) and Formula (IV), the group $R^1$ is hydrogen or methyl. The group Y is a single bond, alkylene, oxyalkylene, or poly(oxyalkylene). The group $R^2$ is a carbocyclic group or heterocyclic group. The group $R^3$ is a linear or branched alkyl.

Embodiment 10 is the article of any of embodiments 1 to 8, wherein the monomer composition further contains a second monomer that is a hydroxyl-containing monomer of Formula (V) or Formula (VI).

$$CH_2{=}CR^1{-}(CO){-}O{-}R^4 \qquad (V)$$

$$CH_2{=}CR^1{-}(CO){-}O{-}R^5{-}O{-}Ar \qquad (VI)$$

In Formula (V) and Formula (VI), the group $R^1$ is hydrogen or methyl. The group $R^4$ is an alkyl substituted with one or more hydroxyl groups or is a group of formula $-(CH_2CH_2O)_qCH_2CH_2OH$ where the variable q is an integer equal to at least 1. The group $R^5$ is an alkylene substituted with at least one hydroxyl group and the group Ar is an aryl group.

Embodiment 11 is the article of any of embodiments 1 to 8, wherein the monomer composition further contains a second monomer having an ionic group.

Embodiment 12 is the article of any of embodiments 1 to 11, wherein the porous polymeric particles include particles in the form of hollow beads.

Embodiment 13 is the article of any of embodiments 1 to 12, wherein an active agent or moisture is adsorbed within at least some of the pores of the porous polymeric particles.

Embodiment 14 is the article of embodiment 13, wherein the active agent includes an antimicrobial agent.

Embodiment 15 is the article of any of embodiments 1 to 14, wherein at least 25% of the porous polymeric particles are fused to the fibrous substrate.

Embodiment 16 is the article of any of embodiments 1 to 15, wherein at least some of the porous polymeric particles are bound to the fibrous substrate with an adhesive, a binder, or a combination thereof.

Embodiment 17 is the article of any of embodiments 1 to 16, wherein the porous polymeric particles have an average diameter in the range of 1 micrometers (μm) to 100 μm.

Embodiment 18 is the article of any of embodiments 1 to 17, wherein the article includes 5 to 90 weight percent porous polymeric particles based on a total weight of the fibrous substrate with the bound porous polymeric particles.

Embodiment 19 is the article of any of embodiments 1 to 18, wherein the article includes 15 to 57 weight percent porous polymeric particles based on a total weight of the fibrous substrate with the bound porous polymeric particles.

Embodiment 20 is the article of any of embodiments 1 to 19, wherein the fibrous substrate includes fibers having an average diameter in a range of from 1 µm to 50 µm.

Embodiment 21 is the article of any of embodiments 1 to 20, wherein the article has an average thickness of from 50 µm to 3,000 µm.

Embodiment 22 is the article of any of embodiments 1 to 21, wherein upon immersion in water for 1 hour, the article does not expand in length in any direction.

Embodiment 23 is a method of making an article that includes a) providing porous polymeric particles; b) providing a fibrous substrate comprising fibers; and c) binding the porous polymeric particles to the fibrous substrate. At least 50% of the porous polymeric particles are bound to the fibrous substrate. The porous polymeric particles include a polymerized product of a reaction mixture that contains i) a monomer composition comprising at least 10 weight percent of a first monomer of Formula (I) based on a total weight of the monomer composition, and ii) a poly(propylene glycol) having a weight average molecular weight of at least 500 grams/mole.

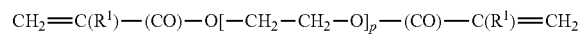
(I)

In Formula (I), the integer p is equal to at least 1 and $R^1$ is hydrogen or alkyl. The poly(propylene glycol) is removed from the polymerized product to provide the porous polymeric particles.

Embodiment 24 is the method of embodiment 23, wherein the binding includes i) heating the fibrous substrate to a temperature above the glass transition temperature of the fibers; ii) contacting the porous polymeric particles with the heated fibrous substrate; and iii) cooling the porous polymeric particles and fibrous substrate to fuse porous polymeric particles to the fibrous substrate.

Embodiment 25 is the method of embodiment 23, wherein the binding the porous polymeric particles to the fibrous substrate is performed simultaneously with the providing a fibrous substrate.

Embodiment 26 is the method of embodiment 25, wherein the binding the porous polymeric particles to the fibrous substrate and the providing a fibrous substrate includes i) extruding meltblown fibers comprising a polymeric material; ii) metering porous polymeric particles into the meltblown fibers; and iii) collecting the meltblown fibers and the porous polymeric particles as a nonwoven fibrous substrate including porous polymeric particles bound to the fibrous substrate.

Embodiment 27 is the method of embodiment 26, wherein the porous polymeric particles are metered using a particle dropper comprising a feed roll.

Embodiment 28 is the method of embodiment 27, wherein a speed of the feed roll is adjusted to regulate the amount of porous polymeric particles bound to the fibrous substrate.

Embodiment 29 is the method of any of embodiments 26 to 28, wherein the meltblown fibers and the porous polymeric particles are collected on a vacuum collection drum roll.

Embodiment 30 is the method of any of embodiments 23 to 29, wherein the fibrous substrate is nonwoven.

Embodiment 31 is the method of any of embodiments 23 to 30, wherein the fibrous substrate includes meltblown fibers.

Embodiment 32 is the method of any of embodiments 23 to 31, wherein the fibrous substrate includes fibers selected from polyolefins, polyesters, polyamides, polyurethanes, rubber elastomers, or combinations thereof.

Embodiment 33 is the method of any of embodiments 23 to 32, wherein the fibrous substrate includes fibers selected from polyethylene, polypropylene, polybutylene, polyethylene terephthalate, polybutylene terephthalate, nylon 6, nylon 66, polyester elastomers, or combinations thereof.

Embodiment 34 is the method of any of embodiments 23 to 33, wherein the fibrous substrate includes fibers having a lower glass transition temperature than the degradation temperature of the porous polymeric particles.

Embodiment 35 is the method of any of embodiments 23 to 34, wherein the reaction mixture contains 1) a first phase having a first volume and comprising i) a compound of Formula (II); and ii) a nonionic surfactant.

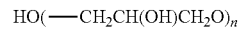
(II)

In Formula (II), the variable n is an integer equal to at least 1. The reaction mixture further contains 2) a second phase having a second volume and being dispersed in the first phase. The first volume is greater than the second volume. The second phase contains i) the monomer composition including at least 10 weight percent of the monomer of Formula (I) based on the total weight of the monomer composition; and ii) the poly(propylene glycol) having a weight average molecular weight of at least 500 grams/mole. The poly(propylene glycol) is removed from the polymerized product to provide the porous polymeric particles.

Embodiment 36 is the method of any of embodiments 23 to 35, wherein the monomer composition further contains a second monomer having one (meth)acryloyl group.

Embodiment 37 is the method of any of embodiments 23 to 36, wherein the monomer composition further contains a second monomer of Formula (III) or Formula (IV).

(III)
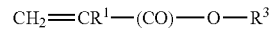
(IV)

In Formula (III) and Formula (IV), the group $R^1$ is hydrogen or methyl. The group Y is a single bond, alkylene, oxyalkylene, or poly(oxyalkylene). The group $R^2$ is a carbocyclic group or heterocyclic group. The group $R^3$ is a linear or branched alkyl.

Embodiment 38 is the method of any of embodiments 23 to 36, wherein the monomer composition further contains a second monomer that is a hydroxyl-containing monomer of Formula (V) or Formula (VI).

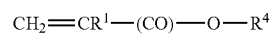
(V)
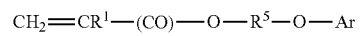
(VI)

In Formula (V) and Formula (VI), the group $R^1$ is hydrogen or methyl. The group $R^4$ is an alkyl substituted with one or more hydroxyl groups or is a group of formula —(CH$_2$CH$_2$O)$_q$CH$_2$CH$_2$OH where the variable q is an integer equal to at least 1. The group R$^5$ is an alkylene substituted with at least one hydroxyl group and the group Ar is an aryl group.

Embodiment 39 is the method of any of embodiments 23 to 36, wherein the monomer composition further contains a second monomer having an ionic group.

Embodiment 40 is the method of any of embodiments 23 to 39, wherein the porous polymeric particles include particles in the form of hollow beads.

Embodiment 41 is the method of any of embodiments 23 to 40, wherein an active agent or moisture is adsorbed within at least some of the pores of the porous polymeric particles.

Embodiment 42 is the method of embodiment 41, wherein the active agent includes an antimicrobial agent.

Embodiment 43 is the method of any of embodiments 23 to 42, wherein at least 25% of the porous polymeric particles are fused to the fibrous substrate.

Embodiment 44 is the method of any of embodiments 23 to 43, wherein at least some of the porous polymeric particles are bound to the fibrous substrate with an adhesive, a binder, or a combination thereof.

Embodiment 45 is the method of any of embodiments 23 to 44, wherein the porous polymeric particles have an average diameter in the range of 1 μm to 100 μm.

Embodiment 46 is the method of any of embodiments 23 to 45, wherein the article includes 5 to 90 weight percent porous polymeric particles based on a total weight of the fibrous substrate with the bound porous polymeric particles.

Embodiment 47 is the method of any of embodiments 23 to 46, wherein the article includes 15 to 57 weight percent porous polymeric particles based on a total weight of the fibrous substrate with the bound porous polymeric particles.

Embodiment 48 is the method of any of embodiments 23 to 47, wherein the fibrous substrate includes fibers having an average diameter in a range of from 1 μm to 50 μm.

Embodiment 49 is the method of any of embodiments 23 to 48, wherein the article has an average thickness of from 50 μm to 3,000 μm.

Embodiment 50 is the method of any of embodiments 23 to 49, wherein upon immersion in water for 1 hour, the article does not expand in length in any direction.

It is to be understood that the invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The following working examples are intended to be illustrative of the present disclosure and not limiting.

EXAMPLES

Unless otherwise noted, all chemicals used in the examples can be obtained from Sigma-Aldrich Corp. (Saint Louis, Mo.). Unless otherwise specified, all microbiological supplies and reagents were purchased as standard products from either Sigma-Aldrich or VWR.

TABLE 1

| Materials | |
|---|---|
| Designation | Description |
| APG 325N | Nonionic alkyl polyglucoside surfactant, obtained from Cognis Corporation (Cincinnati, OH) |
| G3548L | HYTREL ™ G3548L, a thermoplastic poly butylenes/poly(alkylene ether) phthalate available from DuPont (Wilmington, DE, USA) |
| IPA | Isopropyl alcohol, obtained from Sigma Aldrich (St. Louis, MO, USA) |
| IRGACURE 819 | Trade designation for the photoinitiator bis(2,4,6-trimethylbenzoyl)-phenylphosphineooxide, obtained from BASF (Florham Park, NJ, USA) |
| PPG | Polypropylene glycol having a weight average molecular weight of 4000 grams/mole, obtained from Alfa Aesar (Ward Hill, MA, USA) |
| SEMA | Monomer available from Scientific Polymer, Inc. (Ontario, NY, USA) |
| SR 339 | Trade designation for 2-phenoxyethyl acrylate ester obtained from Sartomer Company, Inc. (Exton, PA, USA) |
| SR 6030 | Trade designation for polyethylene glycol 400 dimethacrylate with a weight average molecular weight of 400 grams/mole obtained from Sartomer Company, Inc. (Exton, PA, USA) |

Preparative Example 1 (PE-1): Synthesis of Nanoporous Microparticles

The monomers SR 339 (50 grams), SR 6030 (50 grams) and SEMA (5 grams) were mixed with PPG (43 grams) and IRGACURE 819 (250 milligrams). The mixture was stirred vigorously for 20 minutes on gentle heat of about 40° C. to 50° C. This mixture was then added to 300 grams of glycerol previously mixed with 15 g of the surfactant APG 325N. The mixture was shear mixed for 20 minutes. The mixture was then spread thin between two sheets of polyethylene terephthalate (PET) film which can be obtained from DuPont (Wilmington, Del., USA) under the trade designation ST 500. The mixture was cured with ultraviolet light for 15 to 20 minutes with a 100 Watts, long-wavelength BLACK RAY UV lamp (obtained from UVP, LLC of Upland, Calif., USA) situated at about 15 centimeters (6 inches) from the surface of the material being cured.

The cured mixture was separated from the PET films and then dispersed in excess IPA (500 mL), shaken for 30 minutes, and centrifuged for 10 minutes at 3000 rpm in an EPPENDORF 5810 R centrifuge (obtained from Eppendorf in Germany). The supernatant was removed and the resulting particles were then re-suspended in 500 mL of IPA for a second rinse followed by centrifugation. The particles were again re-suspended in IPA, rinsed and centrifuged. The particles were oven-dried overnight at 70° C. FIG. 4 is a digital SEM image of the particles from PE-1.

Example 1 (EX-1) to Example 4 (EX-4): Meltblown Capture of Nanoporous Microparticles The particle loaded fibrous webs (i.e., fluid management articles) were made using a meltblowing apparatus 20 with a single horizontal stream of filaments as shown in FIG. 6. In this process, the G3548L polymer was extruded through a drilled orifice die 62 at a temperature of 260° C., attenuated by top and bottom air 70 into finer fibers 68, and collected using a vacuum drum roll at a 15 cm die-to-collector distance. The extrusion rate and other processing parameters were adjusted to produce a fibrous web 98 with an effective fiber diameter between 20 and 30 micrometer.

Particles 74 from PE-1 were metered from a hopper 76 using a knurled feed roll 78 onto the horizontal stream of fibers 68 at a distance of 2 to 5 cm from the die tip 67. As the particles 74 dropped on the hot meltblown fibers 68, they were captured by the fibers (see FIG. 7). For each of Examples 1 to 4, the speed of the feed roll was adjusted in order to create webs of different weight percentages of nanoporous microparticles loaded onto the meltblown fibrous web (i.e., EX-1=15 wt. %; EX-2=31 wt. %; EX-3=48 wt. % and EX-4=57 wt. %), where the fibrous web had a weight of 117 to 233 g/m².

TABLE 2

Weight density and particle loading percentages of the meltblown

| Particle-loaded meltblown fibrous web (fluid management article) | Web weight, g/m² | Weight percent of nanoporous particles in the particle-loaded melblown web |
|---|---|---|
| EX-1 | 117 | 15 |
| EX-2 | 145 | 31 |
| EX-3 | 193 | 48 |
| EX-4 | 233 | 57 |

Comparative Example 1 (Comp-1; Control): Meltblown Fibrous Web without Particles A meltblown fibrous web was prepared using the G348L material in the same process Ex-1 to Ex-4 were made, except without particle loading. The particle-free fibrous web had a basis weight of 100 g/m² and a thickness of 270 micrometer.

Water Vertical Wicking Testing

Particle-loaded meltblown materials from EX-1 to EX-4 and comparative example Comp-1 were cut into 1.6 cm by 12 cm strips, and an end of each strip was dipped into a pan holding deionized water. Over a period of 100 seconds, the water wicked up the strips, as summarized in Table 3.

TABLE 3

Vertical wicking of water

| Particle-loaded meltblown material (fluid management article) | Weight percent of nanoporous microparticles in the particle-loaded melblown web | Water wicking distance after 100 seconds, cm |
|---|---|---|
| Comp-1 (control) | 0 | 3.6 |
| EX-1 | 15 | 7.3 |
| EX-2 | 31 | 8.2 |
| EX-3 | 48 | 9.1 |
| EX-4 | 57 | 10 |

The data in Table 3 show that the vertical wicking of water was better with the particle-loaded meltblown materials compared to the control, and improved with higher percentage of nanoporous microparticle loading in the fibrous web.

Water Absorption Testing

Particle-loaded meltblown materials from EX-1 to EX-4 and comparative example Comp-1 were cut into 1.6 cm by 12 cm strips, weighed to obtain a dry weight ("Dry Wt"), and soaked in deionized water for 1 minute. Then the strips were lifted vertically using a prong to drip excess water, held for 1 minute, and then weighed to obtain the wet weight ("Wet Wt"). Percentage absorption was calculated as:

Percentage absorption, %=(Wet Wt–Dry Wt)/Dry Wt×100

The data in Table 4 showed that the absorption capacity of the meltblown web increased by at least three times with the incorporation of the nanoporous particles in the web.

TABLE 4

Water absorption capacity of the particle-loaded meltblown webs (fluid management articles)

| Material | Percentage absorption, wt. % |
|---|---|
| Comp-1 (control) | 47 |
| EX-1 | 174 |
| EX-2 | 228 |
| EX-3 | 255 |
| EX-4 | 283 |

Wicking/Evaporation Performance Testing

Figure 9:
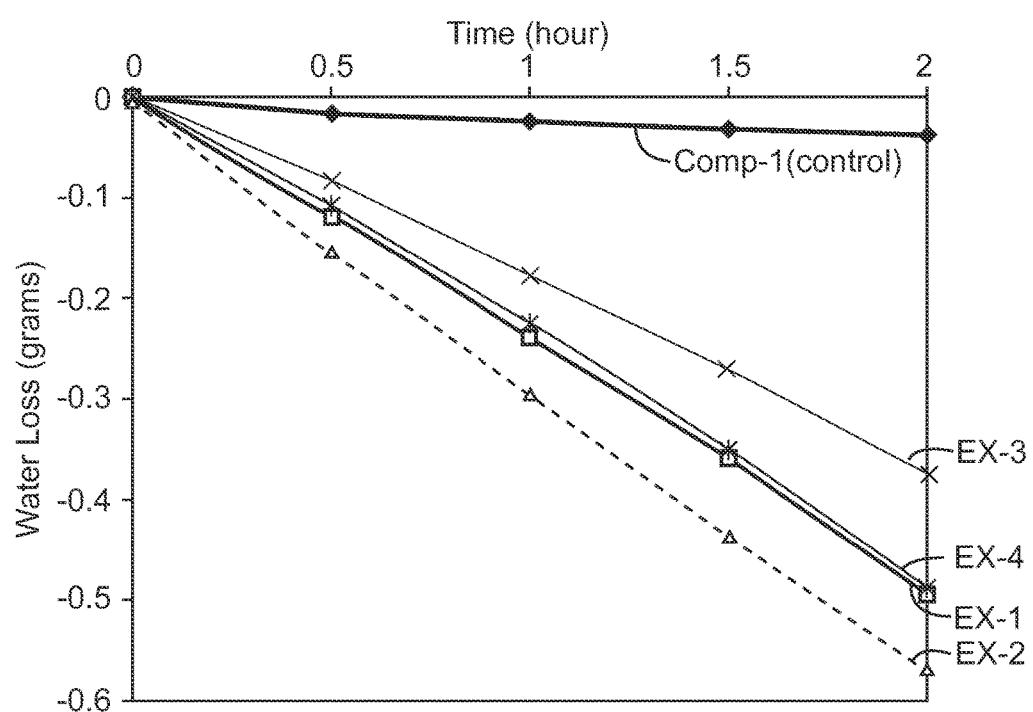
FIG. 9 is a graph of water loss versus time described in the Wicking/Evaporation Performance Testing examples.

Particle-loaded meltblown materials from EX-1 to EX-4 and comparative example Comp-1 were cut into 1.6 cm by 12 cm strips. As shown in FIG. 8, for each strip 42, an end 44 of the strip was inserted through a 0.3 cm by 1.9 cm slit in a bottle cap and then dipped into the bottle 46 containing deionized water 47, while the other end 45 of the strip was extended outside the bottle 46 and taped to a holder 48. The bottle 46 and strip 42 were then placed on a scale 49 that was shielded from the sides and with an open top in room temperature of 23° C. The weight loss was measured every 30 minutes for a period of 2 hours. The water weight loss results were summarized in Table 5, and the weight loss results in Table 5 were also plotted in FIG. 9 to illustrate the water loss versus time.

TABLE 5

Water loss from the wicking/evaporation test

| | Water loss (grams) | | | | |
|---|---|---|---|---|---|
| Material | t = 0 hr | t = 0.5 hr | t = 1 hr | t = 1.5 hr | t = 2 hr |
| Comp-1 (control) | 0 | –0.013 | –0.022 | –0.030 | –0.036 |
| EX-1 | 0 | –0.116 | –0.238 | –0.357 | –0.493 |
| EX-2 | 0 | –0.152 | –0.295 | –0.437 | –0.569 |

TABLE 5-continued

Water loss from the wicking/evaporation test

| Material | Water loss (grams) | | | | |
|---|---|---|---|---|---|
| | t = 0 hr | t = 0.5 hr | t = 1 hr | t = 1.5 hr | t = 2 hr |
| EX-3 | 0 | −0.080 | −0.175 | −0.270 | −0.373 |
| EX-4 | 0 | −0.105 | −0.223 | −0.350 | −0.486 |

Simulated Diaphoretic or Bleeding Episode Testing

Example Wound Dressing

An example wound dressing was prepared having the construction of FIG. 3 by laminating a transparent polyurethane film pattern coated with a 97:3 isooctyl acrylate:acrylamide adhesive (TEGADERM™ film, 3M Company, St. Paul, Minn.) to EX-4, which was previously pattern coated with the same 97:3 isooctyl acrylate:acrylamide adhesive. The pattern-coated polyurethane film provided the backing and backing adhesive of the wound dressing, and the pattern-coated EX-4 provided the fluid management article and adhesive. A window was cut from EX-4 prior to being laminated to the polyurethane film, such that the window could be positioned over sample tubing, and the sample tubing could be observed via the transparent polyurethane film.

Comparative Wound Dressing

A comparative wound dressing was prepared as described above for the 'Example Wound Dressing,' except that the fluid management article (i.e., EX-4) was substituted with a polyester spunlace material (SONTARA® Dupont Corporation, Wilmington, Del.), which was previously pattern coated with the same 97:3 isooctyl acrylate:acrylamide adhesive.

The Example Wound Dressing and the Comparative Wound Dressing were each used to separately secure a ⅛-inch (about 0.3 cm)-diameter tubing to a glass dish, with the most distal end of the tubing (i.e., the tubing exit) being positioned within the window and under the backing. Water, which was died red for better visibility, was pumped through the tubing for 25 minutes at a rate of 0.1 ml/min.

Figure 10:
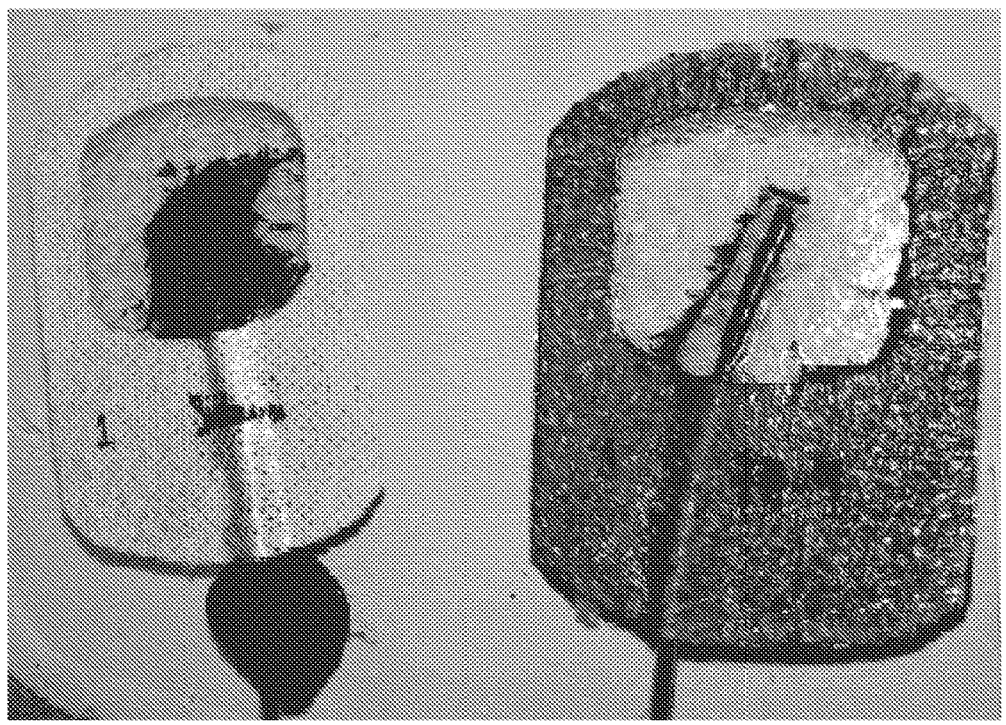
FIGS. 10 and 11 are photographs showing results from the Simulated Diaphoretic or Bleeding Episode Testing, as described in the examples.
Figure 11:

The results are shown in FIGS. 10 and 11, with the Comparative Wound Dressing on the left, and the Example Wound Dressing on the right.

As shown in FIG. 10, the Example Wound Dressing was able to remove the water from the tubing exit and retain it in the fluid management article; whereas, when the Comparative Wound Dressing was employed, the Comparative Wound Dressing did not absorb the water, and water pooled at the tubing exit and leaked from the dressing.

As shown in FIG. 11, when the Comparative and Example Wound Dressings were removed from the glass dish and tubing, substantial water remained on the glass dish surface underneath where the Comparative Wound Dressing had been, as compared to the glass dish surface underneath where the Example Wound Dressing had been.

Similar results were observed with other test fluids, including Ringer's Salt Solution (Ringers solution is made by combining 6.5 g NaCl, 0.42 g KCl, 0.25 g CaCl2 and 1 mole of sodium bicarbonate in one liter of distilled water), and Sheep's blood.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A medical dressing comprising:
   a fluid management article comprising:
   1) a fibrous substrate; and
   2) porous polymeric particles, wherein at least 50% of the porous polymeric particles are bound to the fibrous substrate, wherein the porous polymeric particles comprise a polymerized product of a first monomer of Formula (I)

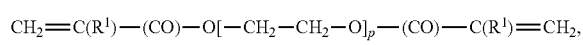

$$CH_2=C(R^1)-(CO)-O[-CH_2-CH_2-O]_p-(CO)-C(R^1)=CH_2,$$

wherein p is an integer equal to at least 1 and $R^1$ is hydrogen or alkyl,
   wherein the product is formed in a reaction mixture comprising:
   a) a first phase having a first volume and comprising
      i) a compound of Formula (II)

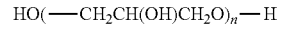

$$HO(-CH_2CH(OH)CH_2O)_n-H$$

wherein n is an integer equal to at least 1, and
      ii) a nonionic surfactant; and
   b) a second phase having a second volume and being dispersed in the first phase, wherein the first volume is greater than the second volume and wherein the second phase comprises;
      i) a monomer composition comprising at least 10 weight percent of the first monomer based on a total weight of the monomer composition, and
      ii) a poly(propylene glycol) having a weight average molecular weight of at least 500 grams/mole, wherein the poly(propylene glycol) used as a porogen does not form a portion of the polymerized product.

2. The medical dressing of claim 1, further comprising a backing configured to cover at least a portion of the fluid management article.

3. The medical dressing of claim 2, wherein the backing includes a compression dressing.

4. The medical dressing of claim 2, wherein the backing includes a first major surface and a second major surface opposite the first major surface, the second major surface comprising a backing adhesive, the backing adhesive being coupled to the first major surface of the fluid management article.

5. The medical dressing of claim 1, wherein the fluid management article includes a first major surface and a second major surface opposite the first major surface, the second major surface comprising a skin-contact adhesive.

6. The medical dressing of claim 5, wherein the skin-contact adhesive is pattern coated on the second major surface of the fluid management article.

7. The medical dressing of claim 5, wherein the skin-contact adhesive is provided by at least a portion of the fibrous substrate.

8. The medical dressing of claim 5, further comprising a backing configured to cover at least a portion of the fluid management article.

9. The medical dressing of claim 8, wherein the backing includes a first major surface and a second major surface opposite the first major surface, the second major surface comprising a backing adhesive, the backing adhesive being coupled to the first major surface of the fluid management article.

10. The medical dressing of claim 9, wherein the backing adhesive comprises an acrylate-based adhesive, and the skin-contact adhesive comprises an acidic adhesive.

11. The medical dressing of claim 1, wherein the fluid management article comprises a particle loading of at least about 10% based on total dry weight of the article.

12. The medical dressing of claim 1, wherein the monomer composition further comprises a second monomer of Formula (III) or Formula (IV)

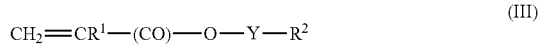 (III)

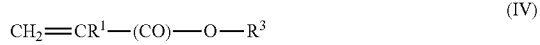 (IV)

wherein
$R^1$ is hydrogen or methyl;
Y is a single bond, alkylene, oxyalkylene, or poly(oxyalkylene);
$R^2$ is a carbocyclic group or heterocyclic group; and
$R^3$ is a linear or branched alkyl.

13. The medical dressing of claim 1, wherein the monomer composition further comprises a second monomer that is a hydroxyl-containing monomer of Formula (V) or Formula (VI),

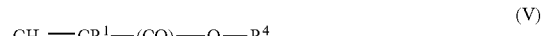 (V)

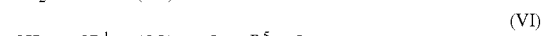 (VI)

wherein
$R^1$ is hydrogen or methyl;
$R^4$ is an alkyl substituted with one or more hydroxyl groups or is a group of formula —$(CH_2CH_2O)_qCH_2CH_2OH$ where q is an integer equal to at least 1; and
$R^5$ is an alkylene substituted with at least one hydroxyl group and the group Ar is an aryl group.

14. The medical dressing of claim 1, wherein an active agent comprising an antimicrobial agent or moisture is adsorbed within at least some of the pores of the porous polymeric particles.

15. The medical dressing of claim 1 wherein at least some of the porous polymeric particles are bound to the fibrous substrate with an adhesive, a binder, or a combination thereof.

16. A method of moving fluid away from a target site, the method comprising applying the medical dressing of claim 1 to the target site, such that the fluid management article is in fluid communication with the target site.

* * * * *

UNITED STATES PATENT AND TRADEMARK OFFICE
CERTIFICATE OF CORRECTION

PATENT NO. : 10,286,100 B2  
APPLICATION NO. : 15/514670  
DATED : May 14, 2019  
INVENTOR(S) : Jennifer Hanson It is certified that error appears in the above-identified patent and that said Letters Patent is hereby corrected as shown below:

In the Specification

Column 12
Line 45, delete "polypropylene" and insert -- poly(propylene --, therefor.

Column 16
Line 3, delete "polypropylene" and insert -- poly(propylene --, therefor.

Column 24
Line 55, delete "polypropylene" and insert -- poly(propylene --, therefor.

Column 35
Line 14, delete "POLYSLIK™," and insert -- POLYSILK™, --, therefor.

Column 39
Line 26, delete "polypropylene" and insert -- poly(propylene --, therefor.

Column 47-48
Line 9 (Table 1), delete "phenylphosphineooxide," and insert -- phenylphosphineoxide, --, therefor.

Column 49
Line 35, delete "melblown" and insert -- meltblown --, therefor.
Line 64, delete "melblown" and insert -- meltblown --, therefor.

Signed and Sealed this  
Third Day of September, 2019

Andrei Iancu  
*Director of the United States Patent and Trademark Office*